(12) United States Patent
Chan et al.

(10) Patent No.: US 8,691,229 B2
(45) Date of Patent: Apr. 8, 2014

(54) METHOD OF PLSCR INHIBITION FOR CANCER THERAPY

(75) Inventors: Err-Cheng Chan, New Taipei (TW); Hong-Arh Fan, Kaohsiung (TW); Kuei-Tien Chen, Guishan Townhip, Taoyuan County (TW); Yung-Bin Kuo, New Taipei (TW); Jinn-Shiun Chen, Taipei (TW); Chung-Wei Fan, Keelung (TW)

(73) Assignee: Err-Cheng CHAN, New Taipei (TW)

( * ) Notice: Subject to any disclaimer, the term of this patent is extended or adjusted under 35 U.S.C. 154(b) by 0 days.

(21) Appl. No.: 13/452,515

(22) Filed: Apr. 20, 2012

(65) Prior Publication Data

US 2013/0280242 A1    Oct. 24, 2013

(51) Int. Cl.
*A61K 38/00* (2006.01)

(52) U.S. Cl.
USPC .............. 424/139.1; 424/143.1; 424/174.1; 424/138.1

(58) Field of Classification Search
None
See application file for complete search history.

(56) References Cited

U.S. PATENT DOCUMENTS

| | | | | |
|---|---|---|---|---|
| 2002/0081698 A1* | 6/2002 | Glucksmann | ................. | 435/194 |
| 2003/0044979 A1* | 3/2003 | Bennett et al. | ................ | 435/455 |
| 2013/0084582 A1* | 4/2013 | Chan et al. | ..................... | 435/7.4 |

OTHER PUBLICATIONS

Sahu et al (Archives of Biochemistry and Biophysics, 2007, 462:103-114).*
Yokoyama et al (Leukemia Research, 2004, 28:149-157).*
Silverman et al (Cancer Research, 2002, 62:397-402).*
Kuo et al (Mol Med, 2011, 17:41-47).*
Fan et al (Journal of Translational Medicine, 2012, 10:254).*
M. Janjundan et al., "Plasma Membrane Phospholipid Scramblase 1 Promotes EGF-dependent Activation of c-Src through the Epidermal Growth Factor Receptor" *The Journal of Biological Chemistry*, vol. 278, No. 39, Sep. 26, 2003, pp. 37413-37418.
J. Sun et al., "c-Abl Tyrosine Kinase Binds and Phosphorylates Phospholipid Scramblase 1" *The Journal of Biological Chemistry*, vol. 276, No. 31, Aug. 3, 2001, pp. 28984-28990.
Y. B. Kuo et al., "Identification of Phospholipid Scramblase 1 as a Biomarker and Determination of its Prognostic Value for Colorectal Cancer" *Mol. Med.* 17(1-2) 41-47, Jan.-Feb. 2011, pp. 41-47.

\* cited by examiner

*Primary Examiner* — Misook Yu
*Assistant Examiner* — Julie Wu
(74) *Attorney, Agent, or Firm* — Muncy, Geissler, Olds & Lowe, P.C.

(57) ABSTRACT

The present invention relates to a method of using inhibitors of phospholipid scramblases (PLSCRs) for the prophylactic or therapeutic treatment of cancers. The PLSCR-inhibitors of the invention comprise compounds PLSCR-specific monoclonal antibodies, antagonists or nucleic acids, which have ability to decrease the level and/or biological activity of PLSCRs in cancer cells.

8 Claims, 20 Drawing Sheets
(3 of 20 Drawing Sheet(s) Filed in Color)

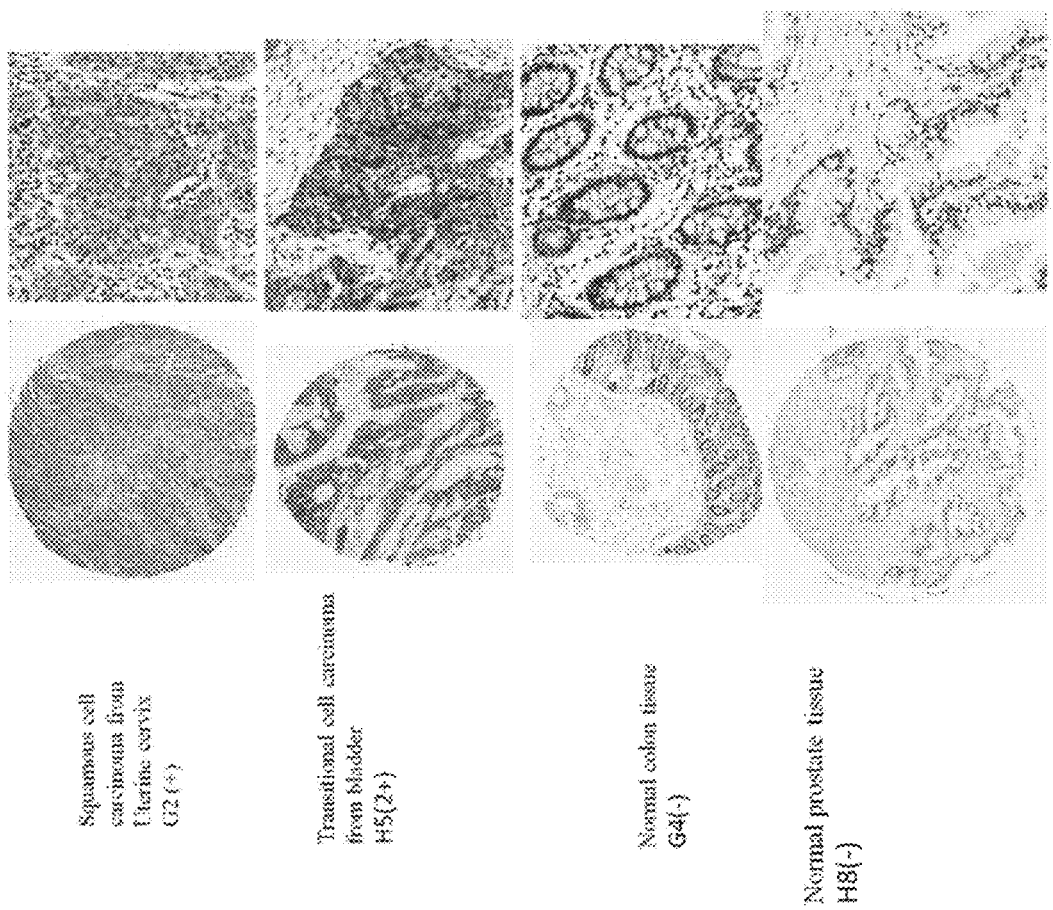

SEQUENCE LISTING

```
<160> NUMBER OF SEQ ID NOS: 4

<210> SEQ ID NO 1
<211> LENGTH: 318
<212> TYPE: PRT
<213> ORGANISM: Homo sapiens
```

```
<400> SEQUENCE: 1

Met Asp Lys Gln Asn Ser Gln Met Asn Ala Ser His Pro Glu Thr Asn
1               5                   10                  15

Leu Pro Val Gly Tyr Pro Pro Gln Tyr Pro Pro Thr Ala Phe Gln Gly
            20                  25                  30

Pro Pro Gly Tyr Ser Gly Tyr Pro Gly Pro Gln Val Ser Tyr Pro Pro
        35                  40                  45

Pro Pro Ala Gly His Ser Gly Pro Gly Pro Ala Gly Phe Pro Val Pro
    50                  55                  60

Asn Gln Pro Val Tyr Asn Gln Pro Val Tyr Asn Gln Pro Val Gly Ala
65                  70                  75                  80

Ala Gly Val Pro Trp Met Pro Ala Pro Gln Pro Pro Leu Asn Cys Pro
                85                  90                  95

Pro Gly Leu Glu Tyr Leu Ser Gln Ile Asp Gln Ile Leu Ile His Gln
            100                 105                 110

Gln Ile Glu Leu Leu Glu Val Leu Thr Gly Phe Glu Thr Asn Asn Lys
        115                 120                 125

Tyr Glu Ile Lys Asn Ser Phe Gly Gln Arg Val Tyr Phe Ala Ala Glu
    130                 135                 140

Asp Thr Asp Cys Cys Thr Arg Asn Cys Cys Gly Pro Ser Arg Pro Phe
145                 150                 155                 160

Thr Leu Arg Ile Ile Asp Asn Met Gly Gln Glu Val Ile Thr Leu Glu
                165                 170                 175

Arg Pro Leu Arg Cys Ser Ser Cys Cys Pro Cys Cys Leu Gln Glu
            180                 185                 190

Ile Glu Ile Gln Ala Pro Pro Gly Val Pro Ile Gly Tyr Val Ile Gln
        195                 200                 205

Thr Trp His Pro Cys Leu Pro Lys Phe Thr Ile Gln Asn Glu Lys Arg
    210                 215                 220

Glu Asp Val Leu Lys Ile Ser Gly Pro Cys Val Val Cys Ser Cys Cys
225                 230                 235                 240

Gly Asp Val Asp Phe Glu Ile Lys Ser Leu Asp Glu Gln Cys Val Val
                245                 250                 255

Gly Lys Ile Ser Lys His Tyr Thr Gly Ile Leu Arg Glu Ala Phe Thr
            260                 265                 270

Asp Ala Asp Asn Phe Gly Ile Gln Phe Pro Leu Asp Leu Asp Val Lys
        275                 280                 285

Met Lys Ala Val Met Ile Gly Ala Cys Phe Leu Ile Asp Phe Met Phe
    290                 295                 300

Phe Glu Ser Thr Gly Ser Gln Glu Gln Lys Ser Gly Val Trp
305                 310                 315

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Asp Lys Gln Asn Ser Gln Met Asn Ala Ser His Pro Glu Thr Asn Leu
1               5                   10                  15

<210> SEQ ID NO 3
<211> LENGTH: 17
<212> TYPE: PRT
```

```
<213> ORGANISM: Artificial Sequence
<220> FEATURE:
<223> OTHER INFORMATION: Synthetic

<400> SEQUENCE: 3

Phe Glu Thr Asn Asn Lys Tyr Glu Ile Lys Asn Ser Phe Gly Gln Arg
1               5                   10                  15

Val

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Thr Gly Ser Gln Glu Gln Lys Ser Gly
1               5
```

METHOD OF PLSCR INHIBITION FOR CANCER THERAPY

FIELD OF THE INVENTION

The present invention relates to a method of using inhibitors of phospholipid scramblases (PLSCRs) for the prophylactic or therapeutic treatment of cancers. The PLSCR-inhibitors include compounds that have ability to decrease the level and/or biological activity of PLSCRs, such as PLSCR1-specific monoclonal antibodies, antagonists and nucleic acids.

BACKGROUND OF THE INVENTION

Cancer is a leading cause of mortality and morbidity. Approaches to treating cancer include surgical intervention to remove tumors and chemotherapy. These approaches can successfully cure some patients. However, even patients that appear to have been cured often suffer a recurrence of the cancer necessitating further therapy. Chemotherapeutic agents generally are nonselective agents that are toxic to cells, such as proliferating cells. Accordingly, such agents may effectively kill cancer cells but also kill healthy cells producing several deleterious side effects.

Certain cancer cells express or overexpress certain cellular components such as cell surface proteins, or express different cellular components when compared to normal cells. One approach to address the short comings of chemotherapeutic approaches to cancer therapy and diagnosis involves targeting cancer cells, for example using antibodies or antibody fragments that bind to proteins that are expressed or overexpressed on cancerous cells. A number of such target proteins have been identified.

Among such proteins scramblase is a protein responsible for the translocation of phospholipids between the two monolayers of a lipid bilayer of a cell membrane. In humans, phospholipid scramblases (PLSCRs) constitute a family of five homologous proteins that are named as hPLSCR1-hPLSCR4. Scramblases are members of the general family of transmembrane lipid transporters known as flippases. The most studied member of this family, phospholipid scramblase 1 (PLSCR1; UniProt accession No. O15162) (a 37 kDa protein), is involved in rapid $Ca^{2+}$ dependent transbilayer redistribution of plasma membrane phospholipids. Recently the function of PLSCR1 as a phospholipids translocator has been challenged and evidences suggest that PLSCR1 acts as signaling molecule. It has been shown to be involved in protein phosphorylation and as a potential activator of genes in response to interferon and other cytokines (Santosh K S et al, *Archives of Biochemistry and Biophysics* 462:103-114, 2007). High-level expression of PLSCR1 when stimulated with IFNs in response to viral infection shows its involvement in cellular immunoresponses. Furthermore, its localization to nucleus with increased synthesis in response to IFNs and binding to promoter of IP3R1 gene to induce its expression show that PLSCR1 plays an essential role in cell differentiation.

In a tissue microarray analysis of PLSCR1 expression in multiple tumor tissues and a few normal tissues (see, FIGS. 7(A)~(D)), it is found that PLSCR1 is highly expressed in many tumor tissues, such as pancreas adenocarcinoma, thyroid medullary carcinoma, esophagus squamous cell carcinoma, esophagus adenocarcinoma, colon adenocarcinoma, rectum adenocarcinoma, uterine cervix squamous cell carcinoma, bladder transitional cell carcinoma; and in normal liver and adrenal gland tissue tissues. Thus, PLSCR1-inhibitors (for example, antibodies, antagonists and siRNA), are developed in the invention and investigated the potential for the treatment of cancers.

SUMMARY OF THE INVENTION

This invention is based on our previous discovery that PLSCR1 is highly expressed in colorectal tumor tissues (Han, C. L., et al, *Molecular & Cellular Proteomics*. 10: 10.1074/mcp.M110.003087,1-15, 2011; and Kuo, Y. B., et al, *Molecular Medicine*. 17(1-2):41-47, 2011), and the unexpected discovery that PLSCR1-inhibitors such as monoclonal antibodies against human PLSCR1 can inhibit the proliferation and neoplastic transformation of cancer cells.

In one aspect, the present invention features a method of using PLSCR-inhibitors for treating and/or preventing cancers. In one embodiment, the PLSCR-inhibitors useful in the method of the invention may be capable of decreasing the biological activity of PLSCR. Examples of such inhibitor include PLSCR-specific ligands, such as monoclonal antibodies and antagonists.

In the embodiments of the invention, the PLSCR-inhibitors represses the activity of the PLSCR family of proteins and the variants of PLSCR. The member of PLSCR family of protein includes PLSCR1, PLSCR2, PLSCR3, and PLSCR4.

The anti-PLSCR antibodies of present invention may be a monoclonal antibody against human PLSCR1 (the polypeptide of SEQ ID NO. 1). In certain embodiments, the monoclonal antibody comprises a protein moiety that has a binding site with binding specificity for a fragment of amino acid 1-160 of human PLSCR1. In certain embodiments, the monoclonal antibody comprises a protein moiety that has a binding site with binding specificity for the C-terminus of human PLSCR1.

In one embodiment, the anti-PLSCR1 antibody is produced in mice using the peptide selected from DKQNSQMNASHPETNL (SEQ ID NO. 2), FETNNKYEIKNSFGQRV (SEQ ID NO. 3), and TGSQEQKSG (SEQ ID NO. 4).

In certain embodiments, methods for treating and/or preventing cancers using a PLSCR-inhibitor may also comprise decreasing the protein level of PLSCR. Decrease of PLSCR protein level can be achieved according to methods known in the art. For example, a siRNA, an antisense nucleic acid, or a ribozyme targeted to PLSCR coding nucleotide sequence can be expressed in the cell.

In another aspect, the invention provides for pharmaceutical compositions comprising a PLSCR1-inhibitor and a pharmaceutically acceptable carrier, diluent or excipient.

The present invention also provides a method of selectively targeting toxicity to cancer cells with high expression level of PLSCR comprising exposing the cancer cells to a therapeutically effective amount of a PLSCR-inhibitor composition of the present invention. A "therapeutically effective amount" means an amount of compound effective to prevent, alleviate or ameliorate symptoms of cancer or prolong the survival of the subject being treated.

In some embodiments, the cancer cell is selected from the cells exhibiting the overexpression of PLSCR, such as a breast cancer cell, a hepatoma cell, a colorectal cancer cell, a pancreatic carcinoma cell, an esophageal carcinoma cell, a bladder cancer cell, an ovarian cancer cell, a skin cancer cell, a gastric cancer cell, a prostate cancer cell, a lung cancer cell, a renal cancer cell, a thyroid cancer cell, a brain cancer cell, melanoma, sarcoma, leukemia, a bone cancer cell and an endometrial cancer cell.

In some embodiments, the present invention provides that the cancer cells are further exposed to at least one additional therapeutic agent selected from the group consisting of anticancer agents, antiviral agents, anti-inflammatory agents and immunosuppressive agents.

The present invention also provides a method of treating or preventing cancer in a subject in need thereof, comprising administering to said subject a therapeutically effective amount of a PLSCR-inhibitor of the present invention. In some embodiments, the PLSCR-inhibitor of the present invention selectively target toxicity to cancer cells with high expression level of PLSCR.

In some embodiments, the cancer is selected from the group consisting of breast cancer, hepatoma, colorectal cancer, pancreatic carcinoma, esophageal carcinoma, bladder cancer, ovarian cancer, skin cancer, gastric cancer, prostate cancer, lung cancer, renal cancer, thyroid cancer, brain cancer, melanoma, sarcoma, leukemia, bone cancer and endometrial cancer.

In some embodiments, application of PLSCR-inhibitor represses the cancer cells through decreasing the activity of Src, Shc, Erks by dephosphorylation. Additionally, the PLSCR-inhibitor represses the cancer cells through decreasing cyclin D1 expression. Finally, the PLSCR-inhibitor represses the cancer cells through reactivating the repressor retinoblastoma by dephosphorylation.

Other features or advantages of the present invention will be apparent from the following drawings and detailed description of several embodiments, and also from the appending claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
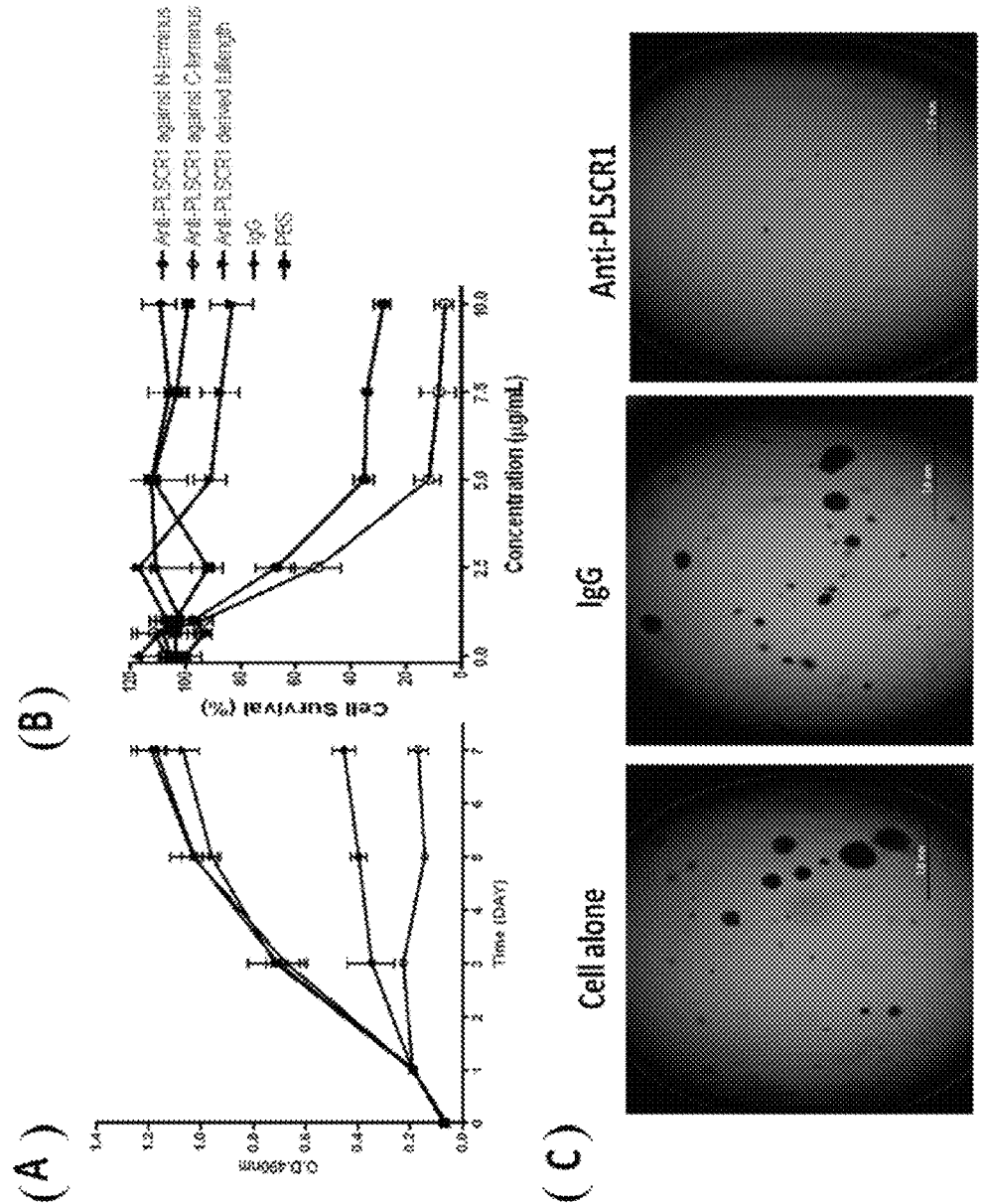
FIG. 1 Anti-PLSCR1 antibody represses the proliferation potential in HT 29 colorectal cancer cell line. (A) The growth curves of HT29 cell line with or without treating with anti-PLSCR1 antibody were compared and results demonstrated slower cell growth for the HT29 cell line with treating with anti-PLSCR1 antibody against the N-terminus or C-terminus epitope of PLSCR1. (B) The proliferative potential of HT29 cells were inhibited by treatment with anti-PLSCR1 antibody against the N-terminus or C-terminus epitope of PLSCR1 in a dose dependent manner. (C) The anchorage-independent colony formation ability of HT29 cells with or without anti-PLSCR1 antibody treatment was compared in the soft agar cell transformation assay.

The present invention concerns inhibitory agent for phospholipid scramblases (PLSCRs) that are useful in the treatment of cancer.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

"PLSCR-inhibitor" refers to a compound that decreases the level of PLSCR protein and/or decreases at least one activity of PLSCR1 protein. In an exemplary embodiment, a PLSCR-inhibiting compound may decrease at least one biological activity of a PLSCR protein by at least about 10%, 25%, 50%, 75%, 100%, or more.

In certain embodiments, methods for reducing, preventing or treating diseases or disorders using a PLSCR-modulating compound may also comprise decreasing the protein level of a PLSCR, or homologs thereof. Decreasing PLSCR protein level can be achieved according to methods known in the art. For example, a siRNA, an antisense nucleic acid, or a ribozyme targeted to the PLSCR can be expressed in or be transfected into the cell. A dominant negative PLSCR mutant, e.g., a mutant that is not capable of phosphorylation, may also be used. Alternatively, agents that inhibit transcription can be used. Methods for modulating PLSCR protein levels also include methods for modulating the transcription of genes encoding PLSCR, methods for destabilizing the corresponding mRNAs, and other methods known in the art.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The present invention concerns antibodies binding to phospholipid scramblase (PLSCR) that are useful in the treatment of cancer. The term "antibody" herein is used in the broadest sense and specifically includes full-length monoclonal antibodies, polyclonal antibodies, multispecific antibodies (e.g., bispecific antibodies), and antibody fragments, as long as they exhibit the desired biological activity. Various techniques relevant to the production of antibodies are provided in, e.g., Harlow, et al., ANTIBODIES: A LABORATORY MANUAL, Cold Spring Harbor Laboratory Press, Cold Spring Harbor, N.Y., (1988)).

As used herein, the term "antibody" means an immunoglobulin molecule or a fragment of an immunoglobulin molecule having the ability to specifically bind to a particular antigen. An "antibody fragment" comprises a portion of a full-length antibody, preferably antigen-binding or variable regions thereof. Examples of antibody fragments include Fab, Fab', $F(ab)_2$, $F(ab')_2$, $F(ab)_3$, Fv (typically the VL and VII domains of a single arm of an antibody), single-chain Fv (scFv), dsFv, Fd fragments (typically the VII and CH1 domain), and dAb (typically a VH domain) fragments; VH, VL, and VhH domains; minibodies, diabodies, triabodies, tetrabodies, and kappa bodies (see, e.g., Ill et al., Protein Eng 1997; 10: 949-57); camel IgG; and multispecific antibody fragments formed from antibody fragments, and one or more isolated CDRs or a functional paratope, where isolated CDRs or antigen-binding residues or polypeptides can be associated or linked together so as to form a functional antibody fragment.

In one embodiment of the invention, the PLSCR-inhibitor is a monoclonal antibody, or binding fragment thereof that specifically binds to the polypeptide sequence of PLSCR1 (SEQ ID NO: 1) and the modified sequence thereof. In some embodiments, the PLSCR1-inhibitor is a monoclonal antibody, or binding fragment thereof that specifically binds to the peptide of SEQ ID NO: 2 and the modified sequence thereof. In other embodiments, the PLSCR1-inhibitor is a monoclonal antibody, or binding fragment thereof that specifically binds to the peptide of SEQ ID NO: 3 and the modified sequence thereof. In further embodiments, the PLSCR1-inhibitor is a monoclonal antibody, or binding fragment thereof that specifically binds to the peptide of SEQ ID NO: 4 and the modified sequence thereof.

In some embodiments of the invention, the monoclonal antibody is a humanized antibody.

In another aspect, the invention relates to a pharmaceutical composition comprising a PLSCR inhibitor as aforementioned; and a pharmaceutically acceptable carrier.

PLSCR-inhibitors can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and re-dissolved or suspended immediately prior to use. Lyophilized forms are also included.

Further in another aspect, the present invention also provides a method of treating or preventing cancer in a subject in need thereof. The claimed methods involve administration of a PLSCR-inhibitor composition of the present invention to a subject, either alone or in combination with an additional therapy such as radiation therapy, chemotherapy or immunomodulatory therapy.

Pharmaceutical compositions for use in accordance with the present invention may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compositions of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compositions can be formulated by combining the active compounds with pharmaceutically acceptable carriers well known in the art. Such carriers enable the compositions of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

EXAMPLES

Example 1

Production of Anti-PLSCR1 Monoclonal Antibodies

Generation of Human PLSCR1-Specific Monoclonal Antibodies

The antibody against PLSCR1 was produced in mice using the peptide DKQNSQMNASHPETNL (SEQ ID NO. 2), which corresponds to residues 2-17 of human PLSCR1 (UniProt accession No. O15162). The peptide was synthesized by Yao-Hong Biotechnology, Inc (New Taipei City, Taiwan, R. O. C.). The anti-PLSCR1 monoclonal antibodies were produced and affinity purified according to previously described procedures by Yao-Hong Biotechnology, Inc (Yu, J. S. et al, Biochem. J. 334: 121-131, 1998). Briefly, 400 µg of peptide was emulsified in complete Freund's adjuvant (Wako chemical), and the emulsion was injected subcutaneously into mice (BALB/cJ). Subsequent inoculations were given at 2-week intervals with 200 µg of peptide in incomplete Freund's adjuvant for three times. The red blood cell-free spleen cells prepared from the mouse immunized with the peptide were fused with the myeloma cells (Fo cell line, Sp2/o-Ag14). Following fusion, the cells are generally resuspended in medium containing HAT (Hypoxanthine, aminopterin and thymidine). The resuspeded cells are transferred into the well of 96-well tissue culture plate. After about 10 days, the wells are screened for the presence of the antibody. Hybridomas secreting the desired antibody are expanded into 24-well plates in preparation for cloning by limiting dilution. After 7-9 days, all wells with clones would be screened. Then, the selected clones would be cloned for a second time. After the second cloning stage, the cells secreting antibody with high titer would be frozen in liquid nitrogen and large quantities of antibody-containing culture supernatants would be produced.

By using the original hydridoma technology, anti-human PLSCR1 monoclonal antibody (N-Terminus) (PN1) was isolated. The isotype of PN1 antibodies was determined using the Monoclonal Antibody Isotyping Kit (Thermo Scientific, USA). The result shows that the isotype of the test antibody was $IgG_1$.

Example 2

Inhibition of the Proliferation and Neoplastic Transformation of Cancer Cells by Anti-PLSCR1 Monoclonal Antibody Cell Culture and Growth Analysis The colorectal cancer (HT29, HCT116 and Colo205), thyroid cancer (CG1), oral cancer (OEC-M1), gastric cancer (AGS), bladder cancer (MGH-U1), lung cancer (A549), and cervical cancer (HeLa) cell lines were maintained at 37° C. in a culture medium supplemented with 10% fetal bovine serum (FBS) and antibiotics in a 5% $CO_2$ incubator. For treatment experiments, cells were split a day before treatment. For observing growth curves, different cell lines were plated at $1\times10^3$ cells per well in 96-well plate and counted in triplicate adding the CellTiter 96® AQueous One Solution Reagent (Promega, Madison, Wis.) to cells.

Antibodies and Reagents

Mouse anti-human PLSCR1 monoclonal antibody (N-Terminus) (IE9) was from LifeSpan BioSciences (LS-C39025, Seattle, Wash.). The mouse isotype IgG was from Jackson ImmunoResearch Laboratories, Inc. (Taipei Hsien, TAIWAN, R. O. C.). HLA Class I antibody (W6/32) was from NOVUS BIOLOGICALS (CO, USA). Alexa Fluor® 488 Goat Anti-Mouse IgG was from Invitrogen Taiwan Ltd (Invitrogen Taiwan Ltd., Taiwan).

Cell Proliferation Assay

Cell proliferation was evaluated with the CellTiter 96® AQueous One Solution Reagent (Promega, Madison, Wis.). The test is based on the ability of mitochondrial dehydrogenase in viable cells to convert MTT reagent into a soluble blue formazan dye. Cells were plated in 96-well plates at the density of $1\times10^3$ cells/well and cultures for the indicated time intervals. Anti-PLSCR1 monoclonal antibody was used at final concentration of 0, 0.65, 1, 2.5, 5, 7.5 and 10 µg/mL. At the end of each incubation, the medium in each well was replaced with fresh medium containing 20 µl of CellTiter 96® AQueous One Solution Reagent into each well, and the plate was incubated for 1 h. After incubation, the relative amounts of formazan were determined by measuring the absorbance at 490 nm using an ELISA reader (Fusion, Packard BioScience Company, CT).

Anchorage-Independent Transformation Assay

Cells (6000/well) in a 6-well plate were exposed to anti-PLSCR1 monoclonal antibody (20 µg/mL, LS-C39025, LifeSpan BioSciences) in 1 mL of 0.5% agar containing 10% FBS over 1 mL of 0.35% agarose containing 10% FBS. The cultures were maintained in a 37° C., 5% $CO_2$ incubator for 14 days. The cells were fed 2 times per week with cell culture media. The 6-well plates were stained with 0.5 mL of 0.005% crystal violet for more than 1 hr. Cell colonies were examined using a dissecting microscope.

Wound Healing Assay

Wound healing assay was performed as following the manufacturer's protocol (ibidi, Martinsried, Germany). Briefly, a culture-insert (ibidi) was transferred to a well of 6-well plates to generate about 500 μm of cell-free gap. A $3.5 \times 10^4$ HT 29 or HCT116 colorectal cancer cells were applied into each well of culture-inserts and incubated at 37° C. and 5% $CO_2$ for 24 hrs. After cell attachment, the Culture-inserts were gently removed by using sterile tweezers. The cells were incubated with medium supplemented with 1% fetal bovine serum (FBS) and treated with anti-PLSCR1 monoclonal antibody (20 μg/mL, LS-C39025, LifeSpan BioSciences). The images of cell-free gap were taken exactly at the same position of the cell culture plate using an inverted microscope (Nikon ECLIPSE TS100, Nikon Instruments Inc., Melville, N.Y.). The cell-covered area was quantified at each time point using Wimasis image analysis platform at https://mywim.wimasis.com/index.php?page=Launch&select=Wound_Healing&gr=ibidi (Munich, Germany).

Matrigel Invasion Assay

Cell invasion was assayed using the QCM ECMatrix Cell invasion assay (Milipore), containing 8 μM pore size polycarbonate membranes with a layer of a reconstituted basement membrane matrix. Cells ($3 \times 10^5$) suspended in 300 μL of serum-free medium were carefully transferred to the upper chambers of the devices and the lower chambers were filled with 500 μL of medium containing 10% fetal bovine serum as an attractant and the chamber was incubated at 37° C. under a humidified 5% $CO_2$ atmosphere for a period of 48 hours. After 48 hours of incubation, non-invading cells were removed from the upper chamber with a cotton swab. The cells that had invaded through polycarbonate membrane to the lower surface were fixed, stained with crystal violet, followed by counting cells with 5 random microscopic fields.

As shown in FIGS. 1(A)~(C), faster cell growth for the HT29 cell line without treating with anti-PLSCR1 antibody; and the proliferative potential of HT29 cells were inhibited by treatment with anti-PLSCR1 antibody in a dose dependent manner. By the data obtained in a soft agar cell transformation assay, indicated that colonies formed by HT29 cells were much larger than those formed by HT29 cells treating with anti-PLSCR1 antibody, suggesting the anchorage-independent colony formation ability of HT29 cells is inhibited by treating with anti-PLSCR1 antibody. These results indicated that application of PLSCR1 inhibitor strongly repress the malignant cell transformation in vitro.

Figure 2:
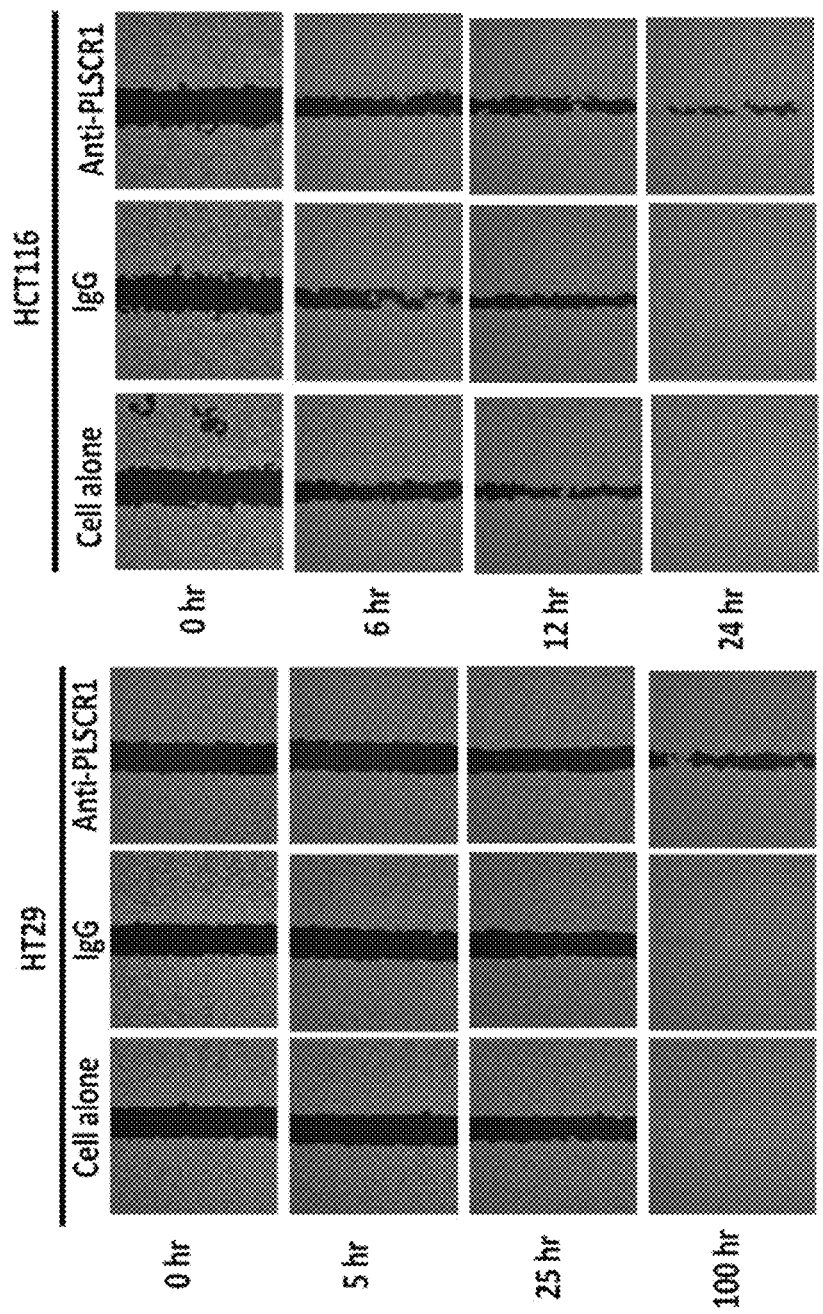
FIG. 2 Effects of anti-PLSCR1 on the migration of HT29 cells and HCT116 cells. Migration assays revealed that the migration capabilities of the two cells treated with anti-PLSCR1 were impaired compared to the cells treated with PBS or IgG. The mouse isotype IgG (209-005-082) (designated as IgG) was from Jackson ImmunoResearch Laboratories, Inc. (Taipei Hsien, TAIWAN, R. O. C.).

Wound healing assay revealed that the migration capabilities of the two colorectal cancer cells treated with anti-PLSCR1 monoclonal antibody were impaired compared to the cells treated with PBS or isotype IgG (FIG. 2).

Figure 3:
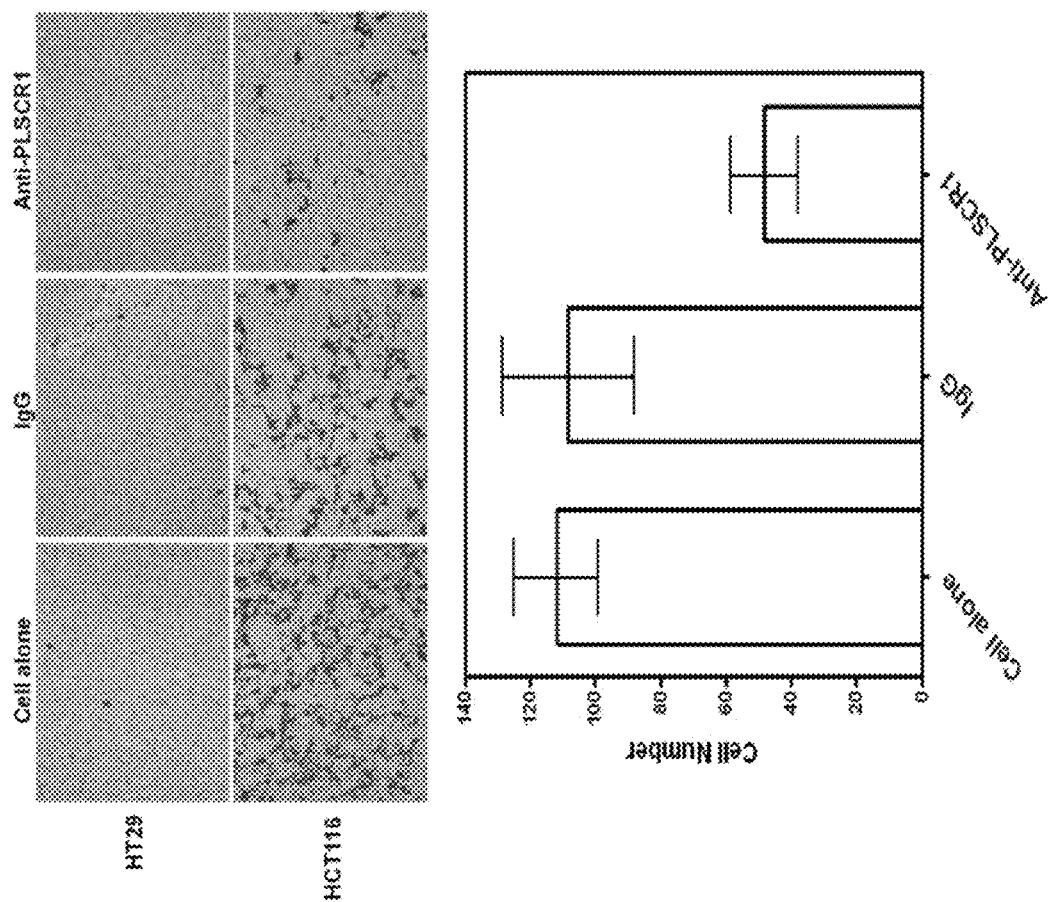
FIG. 3 Effects of anti-PLSCR1 on the invasion of HCT116 cells. Invasion assays of HT29 and HCT116 cells were examined. Representative microphotographs of filters (upper panel) and quantitative analysis of the assay of HCT116 cells results (lower panel) are shown. Each bar represents the mean±SD calculated from three independent experiments.

Trans-well invasion assays further revealed that the invasion capabilities of the HCT116 colorectal cancer cells (derived from a Dukes' stage D patient) treated with anti-PLSCR1 antibody were severely impaired compared to the cells treated with PBS or isotype IgG (FIG. 3); there were ~55% reductions in the invasive abilities of cells treated with anti-PLSCR1 antibody.

Figure 4:
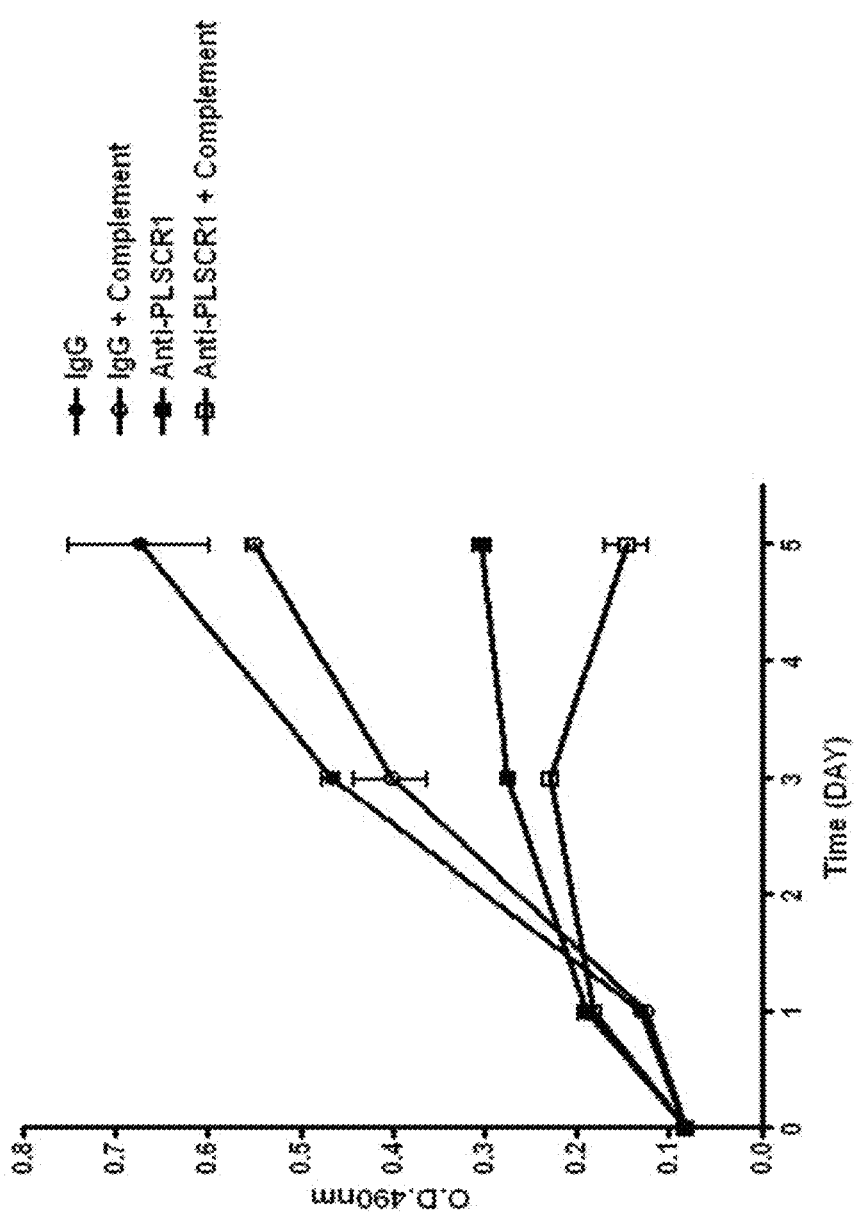
FIG. 4 Complement-dependent cytotoxicity was evaluated by treated HT29 cells with anti-PLSCR1 supplemented with mouse serum. Complement derived from mouse serum in culture medium partially contributes to the inhibition derived from anti-PLSCR1.
Figure 5:
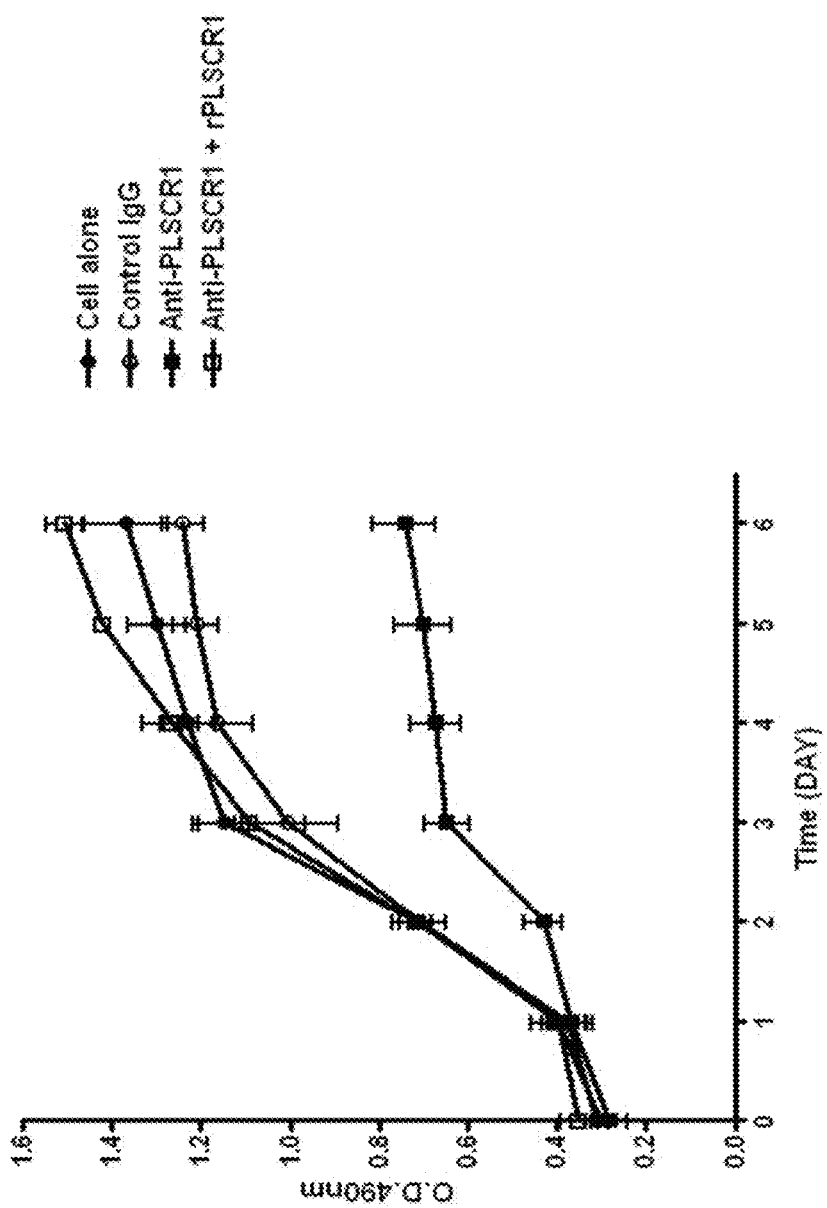
FIG. 5 Blocking the binding activity of anti-PLSCR1 antibody with recombinant PLSCR1 reduces inhibition properties in vitro.
Figure 6:
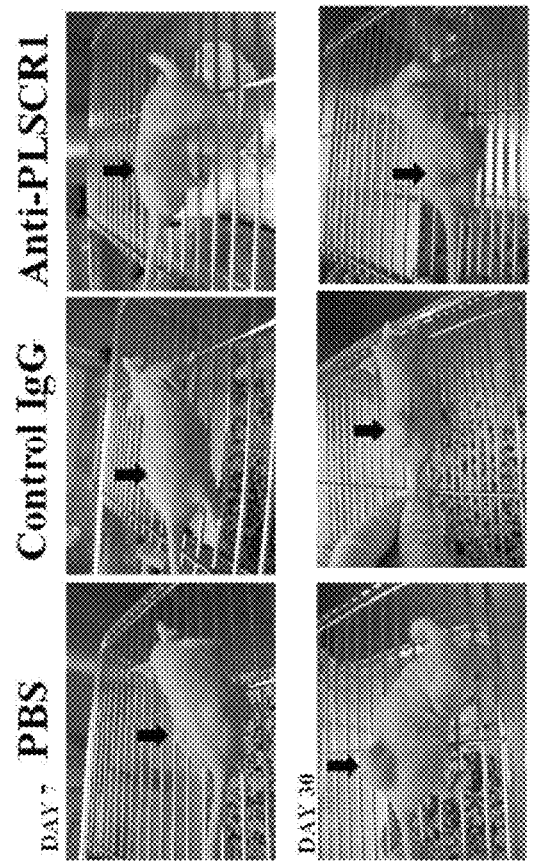
FIG. 6(A) A representative photograph of a mouse from each group at day 7 and day 30 was shown.
FIG. 6(B) Anti-PLSCR1 resulted in inhibiting neoplastic transformation in vivo. Tumors dissected from each group are shown below.
FIG. 6(C) Tumor growth curve of anti-PLSCR1 resulted in inhibiting neoplastic transformation in vivo.
FIG. 6(D) Anti-PLSCR1 resulted in inhibiting neoplastic transformation in vivo. Final average tumor weight of mice treating with isotype IgG or treating with anti-PLSCR1 antibody.
Figure 6:
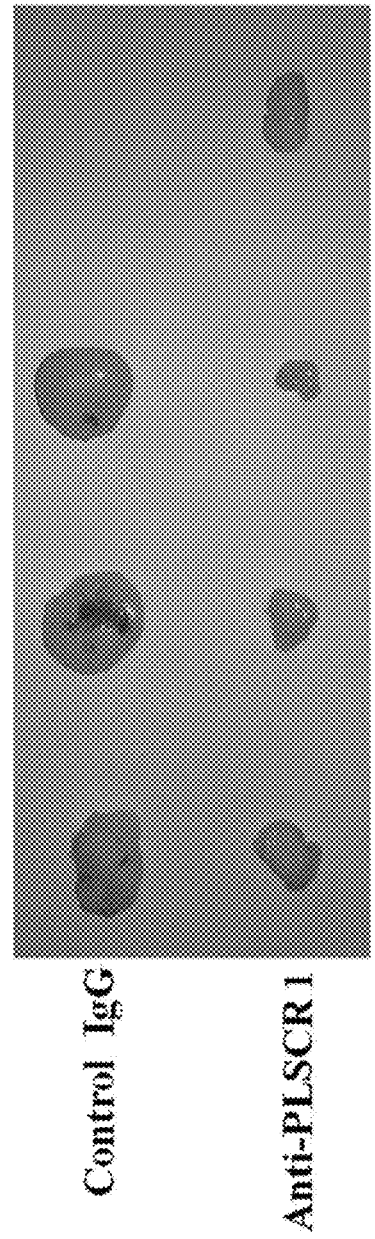
Figure 6:
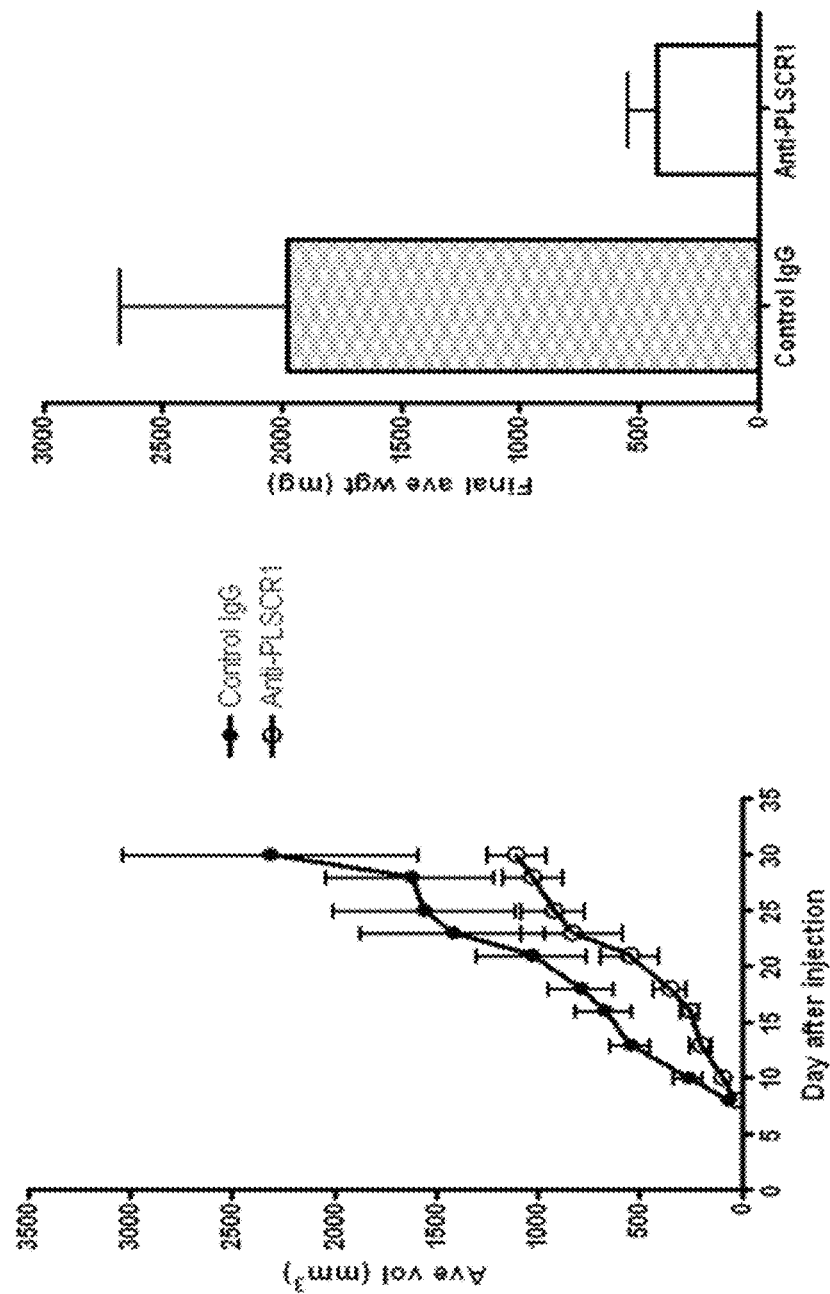
Figure 7:
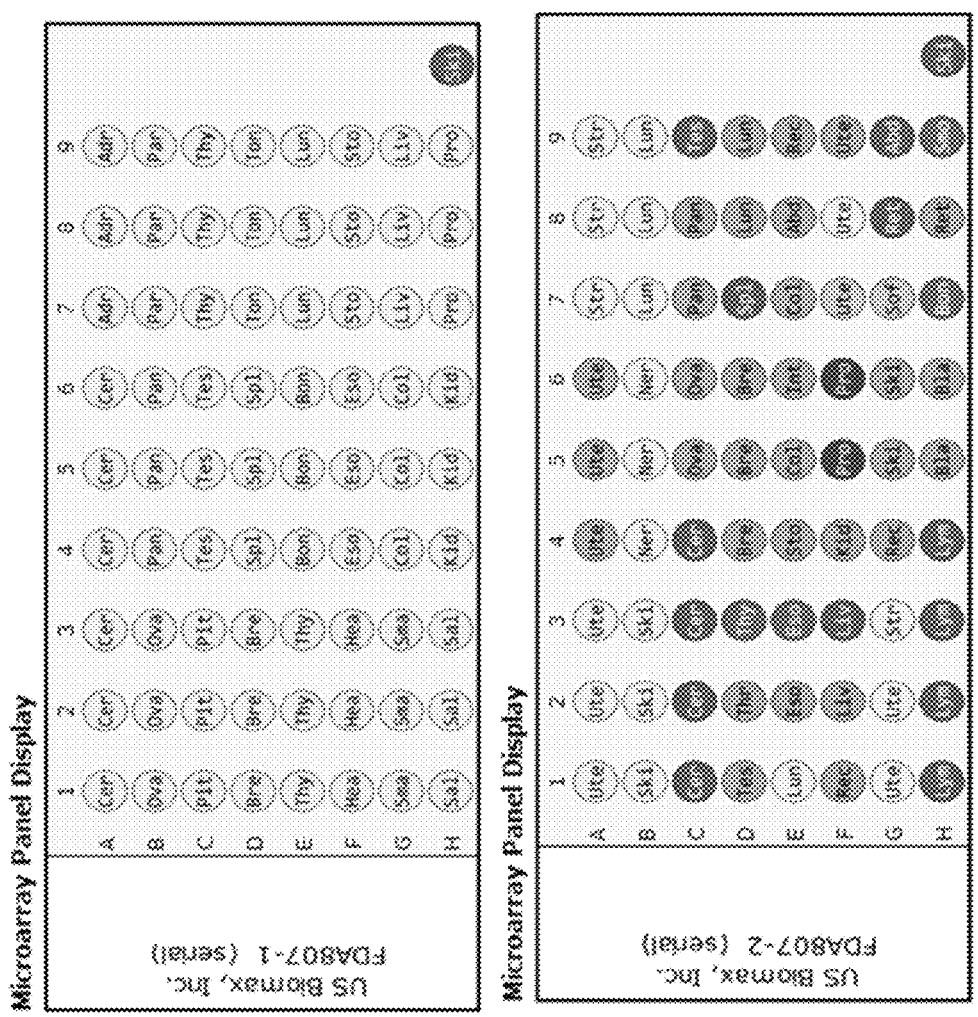
FIG. 7(A) Assessment of PLSCR1 expression by immunohistochemistry tissue array in multiple normal and tumor tissues using a commercially available array (Biomax).
FIG. 7(B) The PLSCR1 expression results indicated that PLSCR1 protein was highly expressed in thyroid medullary carcinoma, colon adenocarcinoma, and bladder transitional cell carcinoma. Several low expressions were also discovered, including normal adrenal gland tissue, normal liver tissue, pancreas adenocarcinoma, esophagus adenocarcinoma, rectum adenocarcinoma, and cervix squamous cell carcinoma.
FIG. 7(C) The relative expression level of PLSCR1 protein in tissue arrays is shown as representative examples of colon, bladder, and rectum tissues.
FIG. 7(D) The relative expression level of PLSCR1 protein in tissue arrays is shown as representative examples of uterine cervix squamous cell carcinoma, bladder transitional cell carcinoma, normal colon, and normal prostate tissues.
Figure 7:
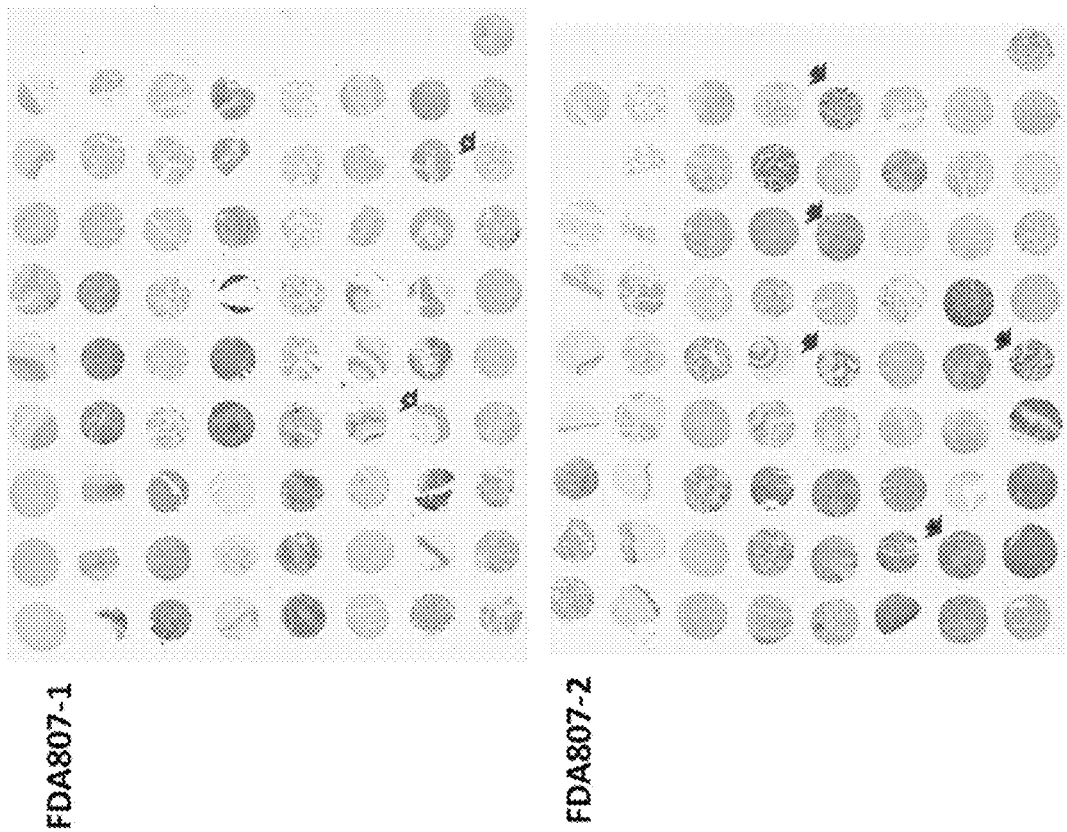
Figure 7:
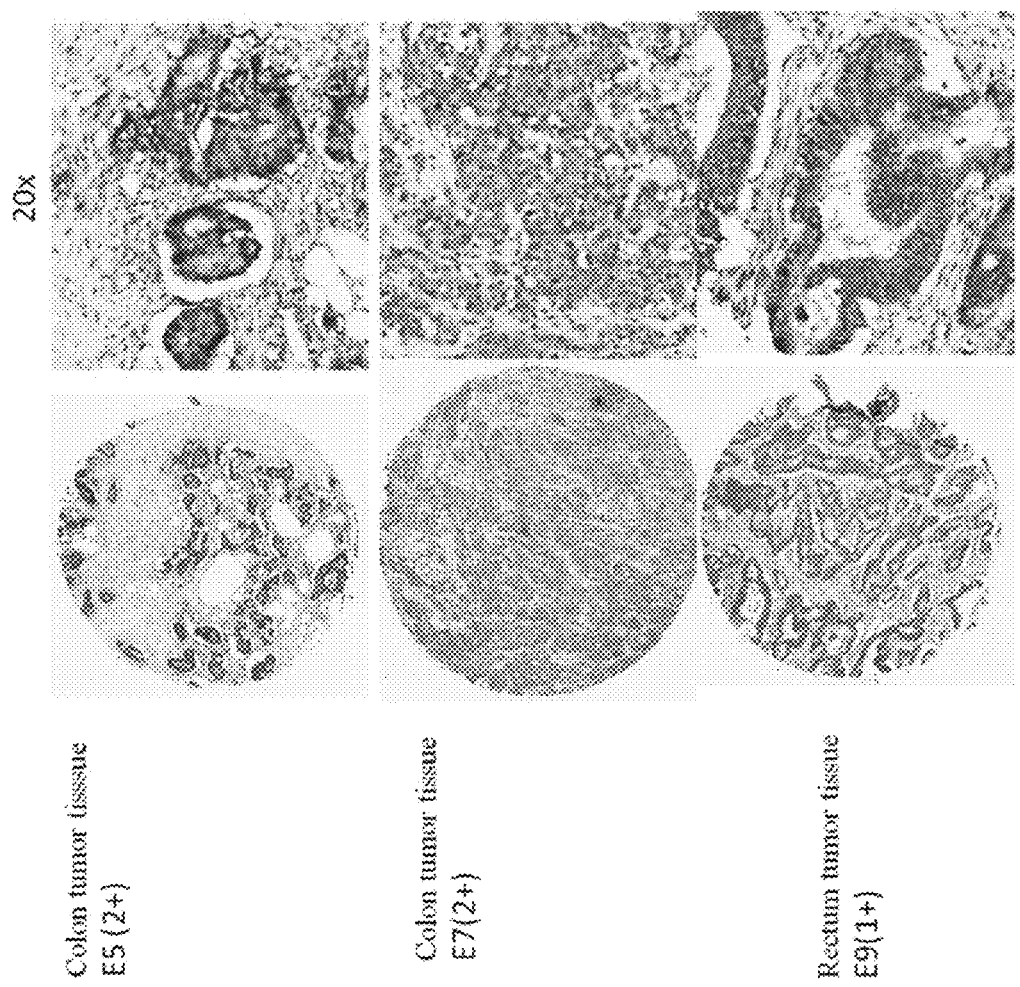

The results shown in FIG. 4 suggested that both complement-mediated and complement-independent mechanisms could contribute to the reduced proliferation in HT29 cells. FIG. 5 shows that blocking of anti-PLSCR1 antibody activity in HT29 colorectal cancer cells reduces inhibition properties of cell growth in vitro.

Example 3

Anti-PLSCR1 Antibody Resulted in Inhibiting Neoplastic Transformation In Vivo

Tumor Xenografts

Athymic Balb/c nude mice (NU/NU mice, female, 5-week-old) were purchased from BioLASCO Taiwan Co., Ltd (Yi-Lan, Taiwan). The HT29 cells ($2 \times 10^6$ in 200 μL phosphate buffered saline) was injected subcutaneously into the left side of athymic Balb/c nude mice, and tumor growth was monitored. Tumor volume (V) was estimated from the length (l), width (w), and height (h) of the tumor using the following formula: $V = 0.52$ ($l \times w \times h$). (Tomayko M M, Reynolds C P., *Cancer Chemother Pharmacol* 24:148-154, 1989)

Treatments were initiated on the seventh day after tumor cell inoculation (at a time when tumor nodules were palpable). All mice were randomized into three groups with 3-4 mice per group, and administered anti-PLSCR1 monoclonal antibody (20 μg/dose, control IgG (20 μg/dose) or PBS once every two days in a volume of 200 μL for a total of three administrations. The tumor model mice were treated by injection at the neighboring location of tumor nodules. Mice were monitored until day 30 after inoculation, at which time mice were killed. Tumors were dissected and weighed and then sent for histochemical analysis. All animal experiments were performed using protocols approved by the Institutional Animal Care and Use Committee (IACUC) of Chang Gung University, and the Committee recognizes that the proposed animal experiment follows the guideline as shown in the Guide for Laboratory Animal Facilities and Care as promulgated by the Council of Agriculture, Executive Yuan, R. O. C.

FIGS. 6(A)~(D) shows the tumor growth curve and final average tumor weight of mice treating with isotype IgG or treating with anti-PLSCR1 monoclonal antibody. The tumor in mice treated with anti-PLSCR1 monoclonal antibody was significantly minished.

Example 4

Tissue Microarray Analysis of PLSCR1 Expression in Multiple Normal and Tumor Tissues Immunohistochemical Analyses for Tissue Array Tissue array specimens of normal and tumor organ tissues were purchased from Biomax (Rockville, Md.). Following the manufacturer's protocol, immunohistochemistry was performed on tissue array specimens using the DAB detection kit (DAKO, AR155, Glostrup, Denmark).

The PLSCR1 antibody was used (1:100) in the immunohistochemical analyses. Expression of the PLSCR1 was categorized as positive or negative and was evaluated according to the simplified H score system (Ravn V, et al, *Pathol Res Pract* 189:1015-22, 1993), which is based on the percentage of cells stained (3, ≥90%; 2, 50-89%; 1, 10-49%; or 0, 0-9%) and the intensity of cell staining (3, strong; 2, moderate; 1, weak; or 0, no cell staining). The 2 scores were multiplied by each other and divided by 3 to obtain the final score. Positive staining was defined as a final score ≥1.

The results as shown in FIGS. 7(A)~(D) indicated that PLSCR1 protein was highly expressed in thyroid medullary carcinoma, colon adenocarcinoma, and bladder transitional cell carcinoma. Several low PLSCR1 expression also was discovered, including normal adrenal gland tissue, normal liver tissue, pancreas adenocarcinoma, esophagus adenocarcinoma, rectum adenocarcinoma, and cervix squamous cell carcinoma.

Figure 10:
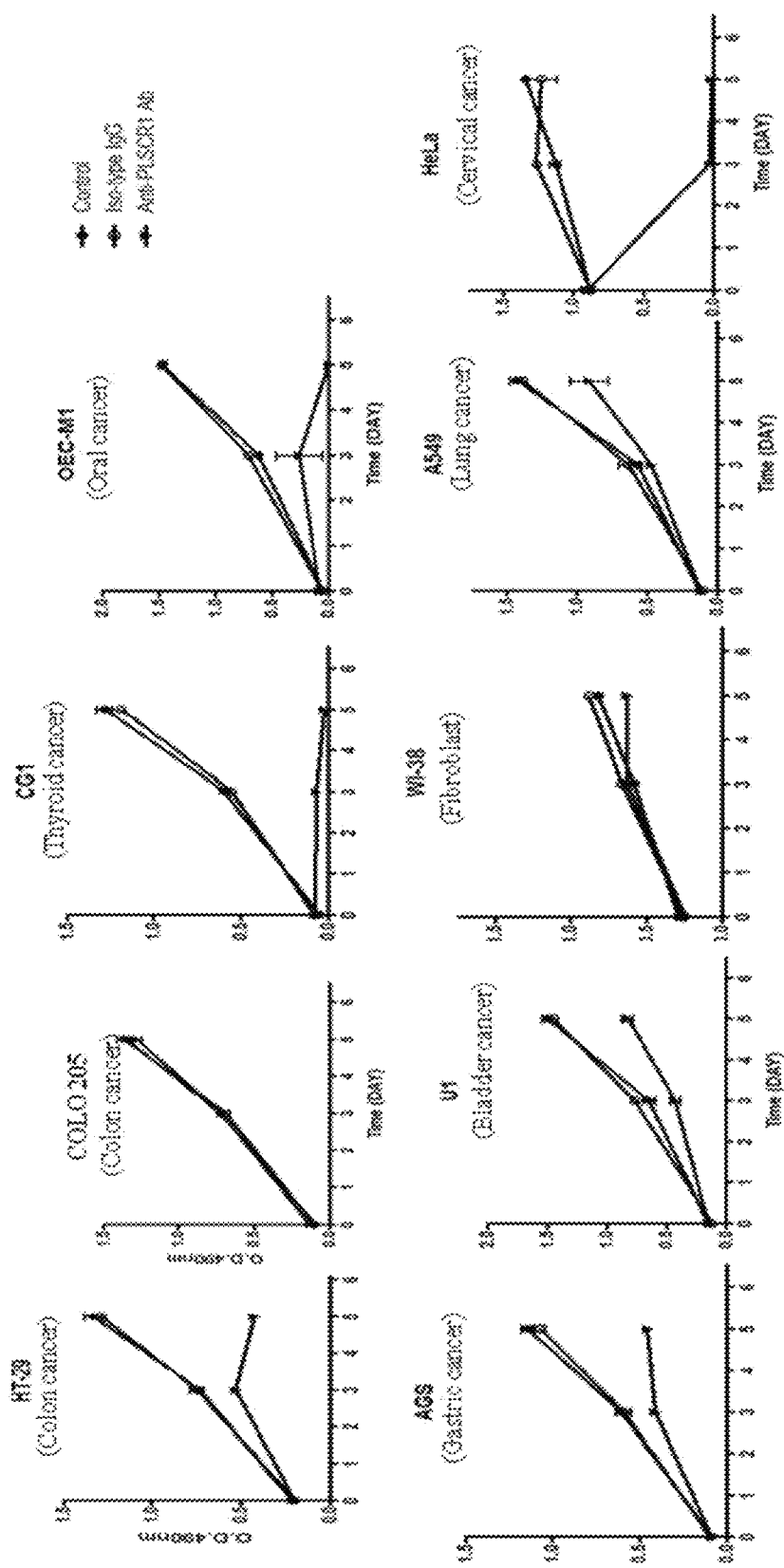
FIG. 10(A) The growth curves of cells treated with PBS, iso-type antibody and anti-PLSCR1 antibody were shown. The significantly effect on inhibition were appeared in HT29 colon cancer, CG1 thyroid cancer, OEC-M1 oral cancer, AGS gastric cancer, MGH-U1 bladder cancer, A549 lung cancer and HeLa cervical cancer cells.
FIG. 10(B) Western blot analysis to determine PLSCR1 protein expression levels in different cell extracts. Actin was applied as loading control. For quantification of western blot experiments, Columns and error bars represent the mean±SD of 3 independent experiments for PLSCR1 and Actin.
Figure 10:
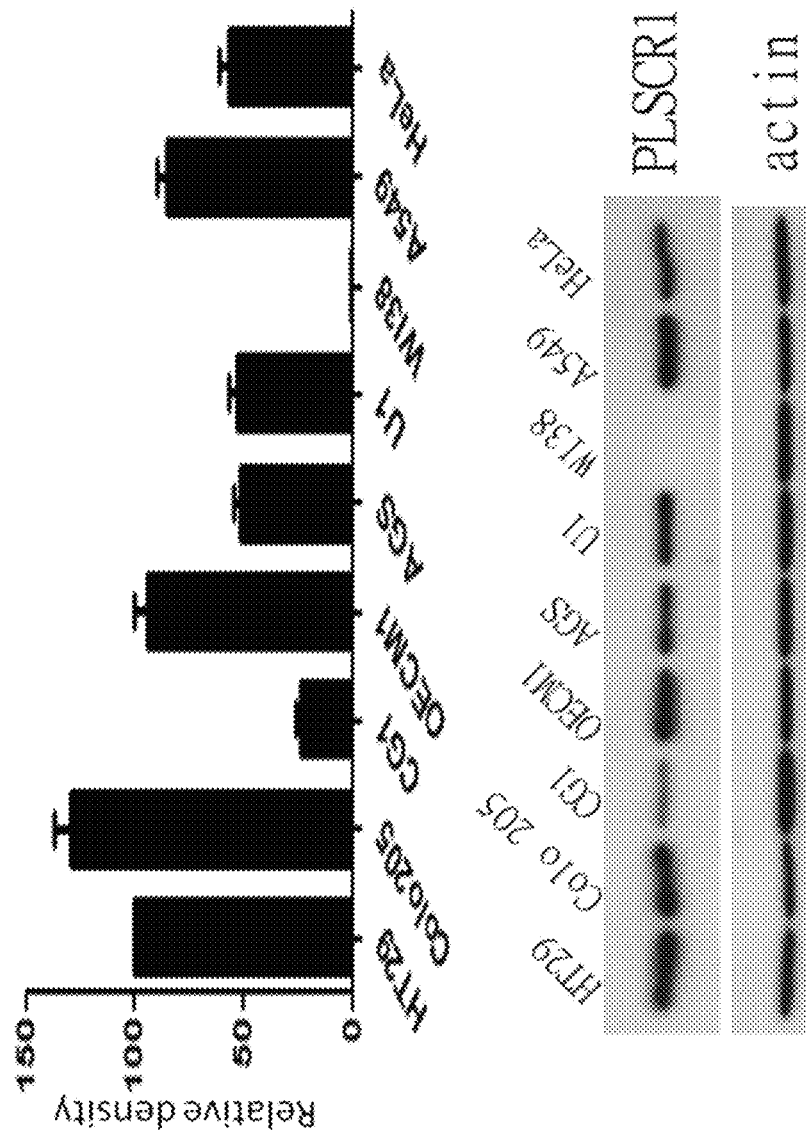
Figure 11:
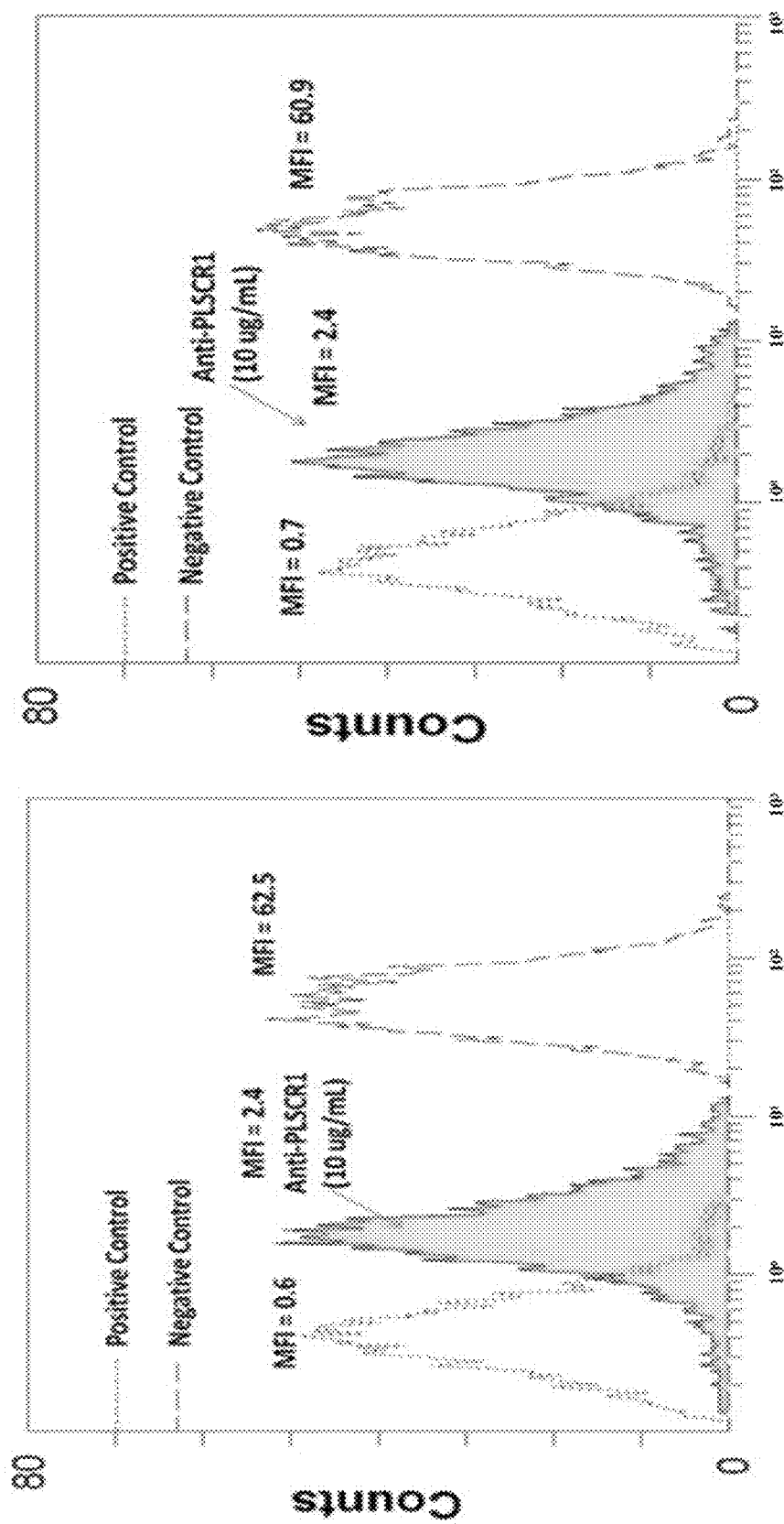
FIG. 11(A) Positive control HLA Class I antibody and anti-PLSCR1 antibody was incubated with PBMC cells at a concentration of 10 μg/mL. Immunofluorescence assay of anti-PLSCR1 or HLA Class I antibody on PBMC cells by flow cytometry with the secondary Alexa Fluor® 488 Goat Anti-Mouse IgG. Area under dotted-line represents PBMC reacted with secondary antibody alone (left panel; negative control), anti-PLSCR1 (middle) and anti-HLA Class I antibody (right panel). The assay were performed from 2 individual subjects.
FIG. 11(B) PBMCs treated with 5, 10, and 20 μg/mL anti-PLSCR1 antibody were evaluated by flow cytometry as described above.
FIG. 11(C) The results showed the fluorescence of RBCs treated with anti-human CD47 antibody or anti-PLSCR1 antibody at a concentration of 10 μg/mL.
FIG. 11(D) RBCs treated with 5, 10, and 20 μg/mL anti-PLSCR1 antibody were examined.
Figure 11:
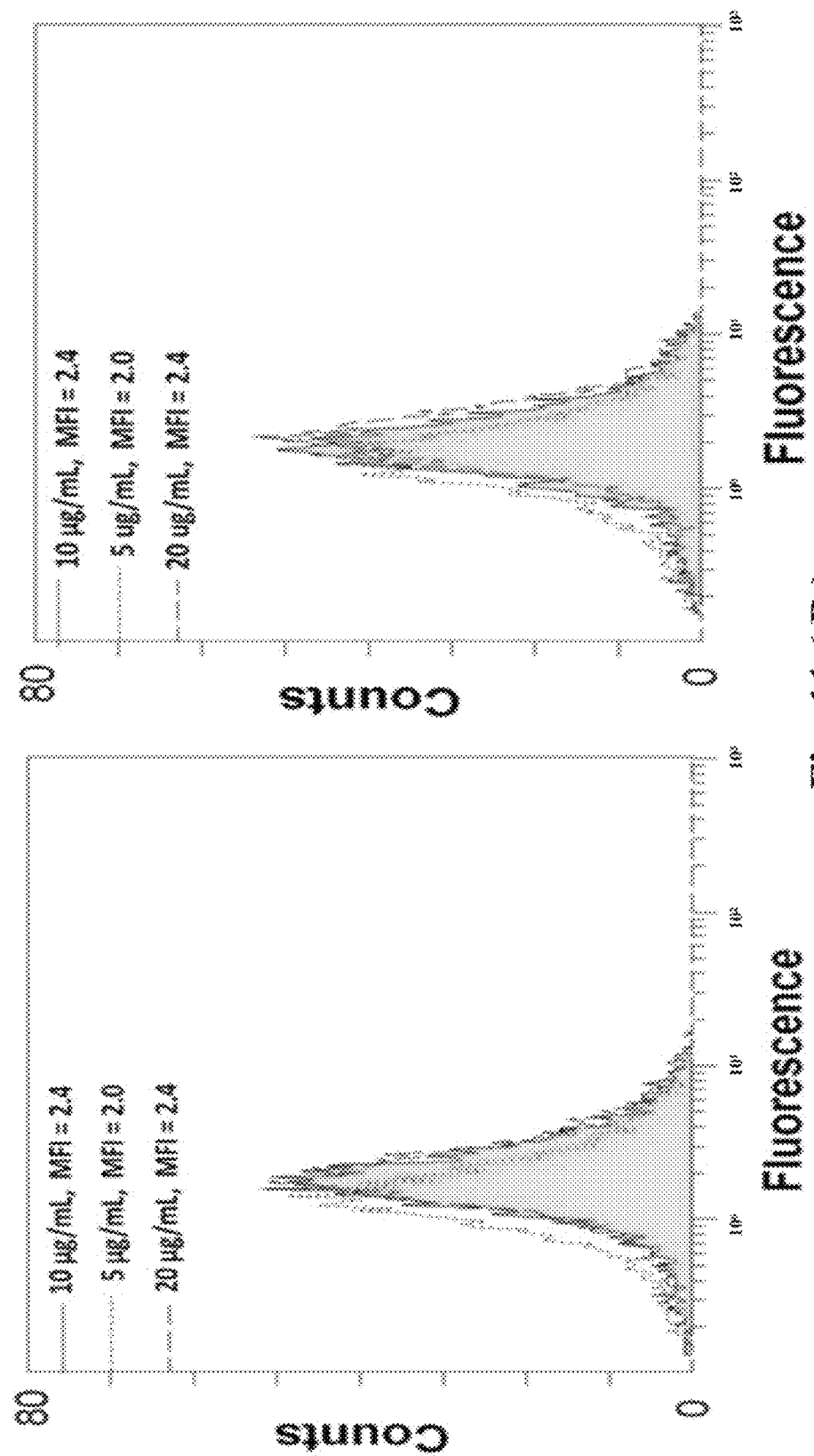
Figure 11:
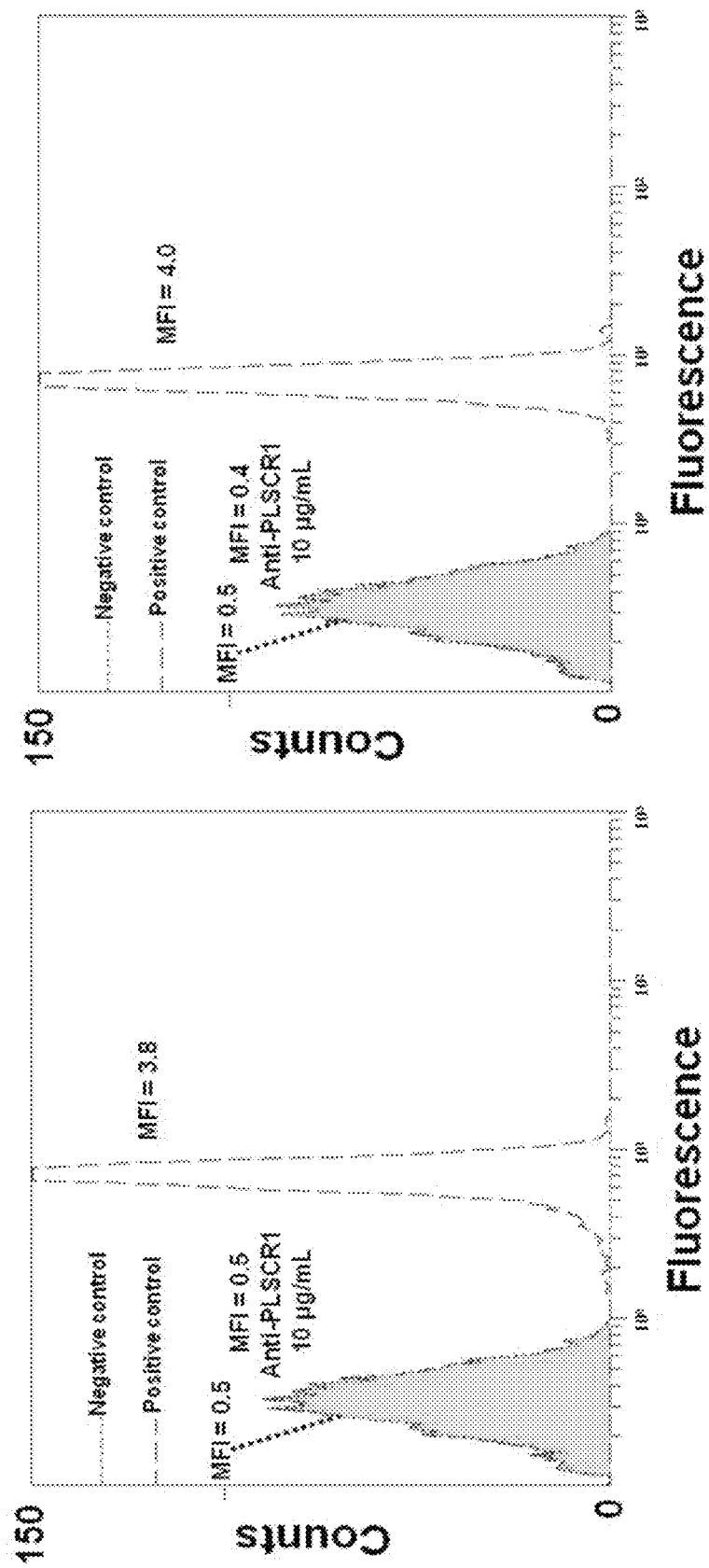
Figure 11:
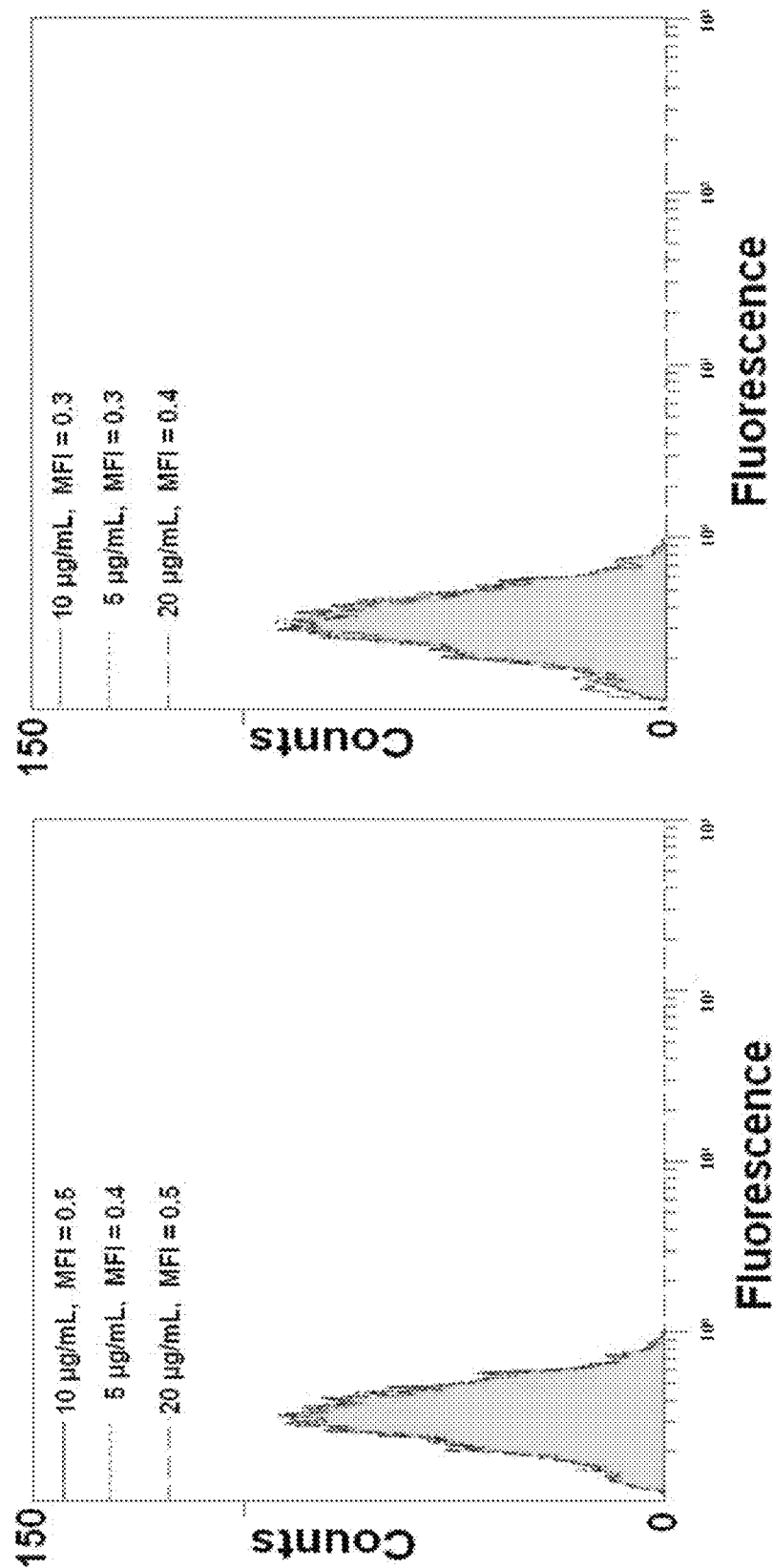

The results as shown in FIG. 10(A) and FIG. 10(B) indicated that the anti-PLSCR1 significantly inhibited the cell growth, including colon cancer (HT29), thyroid cancer (CG1), oral cancer (OEC-M1), gastric cancer (AGS), bladder cancer (MGH-U1), lung cancer (A549) and cervical cancer (HeLa) cells.

Example 5

Observing the Potential Role of PLSCR1 in Signaling Pathway

Western Blotting Analysis

Clinical tissue specimens were taken from freshly isolated surgical resections, snap frozen in liquid nitrogen, and then stored at −80° C. until use. For the analysis of PLSCR1 expression in CRC tissues, frozen tissues were thawed and resuspended in lysis solution (0.25 mol/L sucrose, 10 mmol/L Tris-HCl pH 7.6, 1 mmol/L $MgCl_2$, 1% sodium dodecyl sulfate [SDS] with protease inhibitors (20 μg/μL aprotinin, 20 μg/μL leupeptin, and 1 mmol/L phenylmethanesulfonyl fluoride; protein:protein inhibitor was 100:1, v/v)). The samples were sonicated and centrifuged at 14,000 rpm for 10 minutes. The quantity of protein was determined by DC™ protein assay method (BIO-RAD, Bio-Rad Laboratories, Inc., CA). The samples (50 μg protein) was mixed with electrophoresis sample buffer containing 2% SDS and 5% 2-mercaptoethanol and boiled for 5 min. Proteins were separated by electrophoresis on 12% denaturing polyacrylamide gels and transferred to PVDF membranes (Pall Europe Ltd., Portsmouth, UK). The blots were blocked with 5% skim milk and then probed with anti-human PLSCR1 monoclonal antibodies at a dilution of 1:1000 for 2 h at room temperature, followed by incubation for 1 h with peroxidase-conjugated secondary antibody at room temperature. The blots were developed with enhanced chemiluminescence (ECL) western reagents and exposed to Kodak Biomax light films. The immunoblot images were acquired by Imagemaster (Amersham Pharmacia Biotech, Piscataway, N.J.). The protein level of each band was quantified by densitometry and analyzed with Multi Gauge Version 2.0 software (Fuji PhotoFilm, Tokyo, Japan). Data were analyzed with a paired t-test using the statistical software SPSS/Windows 12.0 statistical package (SPSS, Inc., Chicago, Ill.). $P<0.05$ was considered statistically significant.

Figure 8:
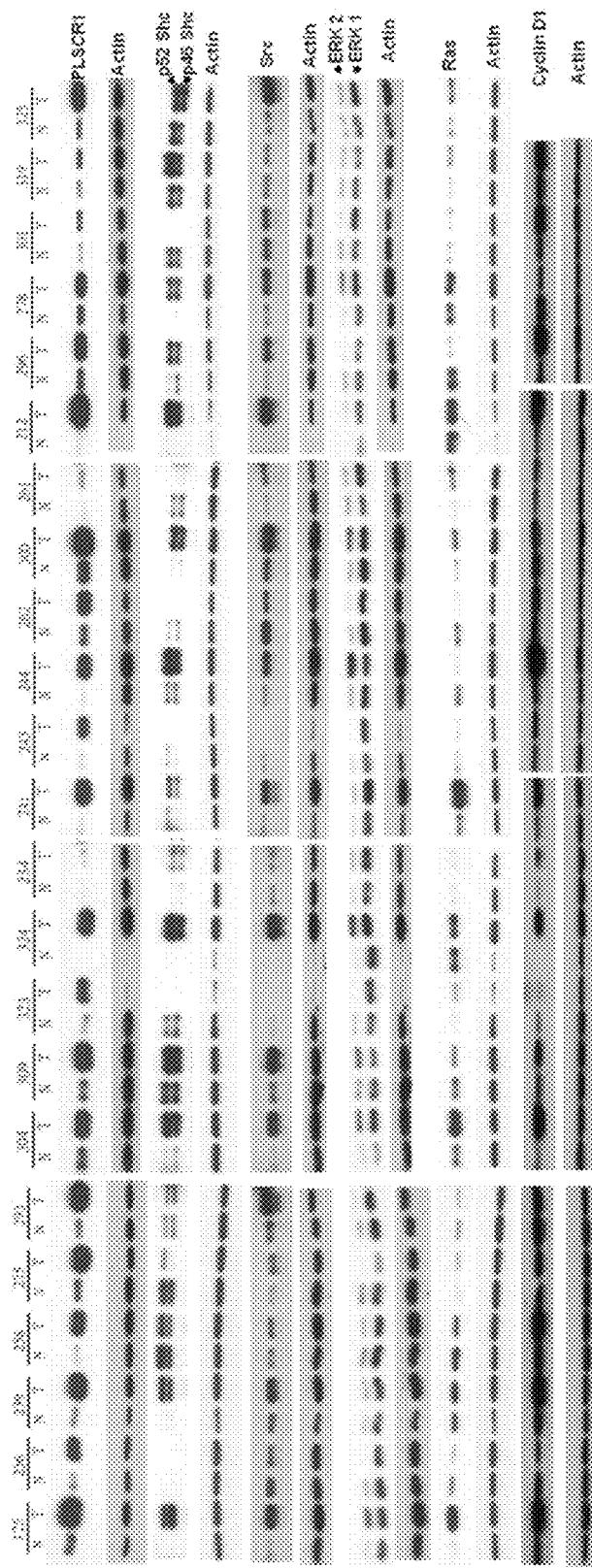
FIG. 8(A) Western blot analysis of PLSCR1, Shc, Src, Erk and Ras and cyclin D1 expression levels in colorectal tissue pairs. The fold-changes of each protein in tumor versus normal tissues were evaluated by two-sided t test ($p<0.05$).
FIG. 8(B) The raw data points were presented as scatter plot and the mean values were indicated.
Figure 8:
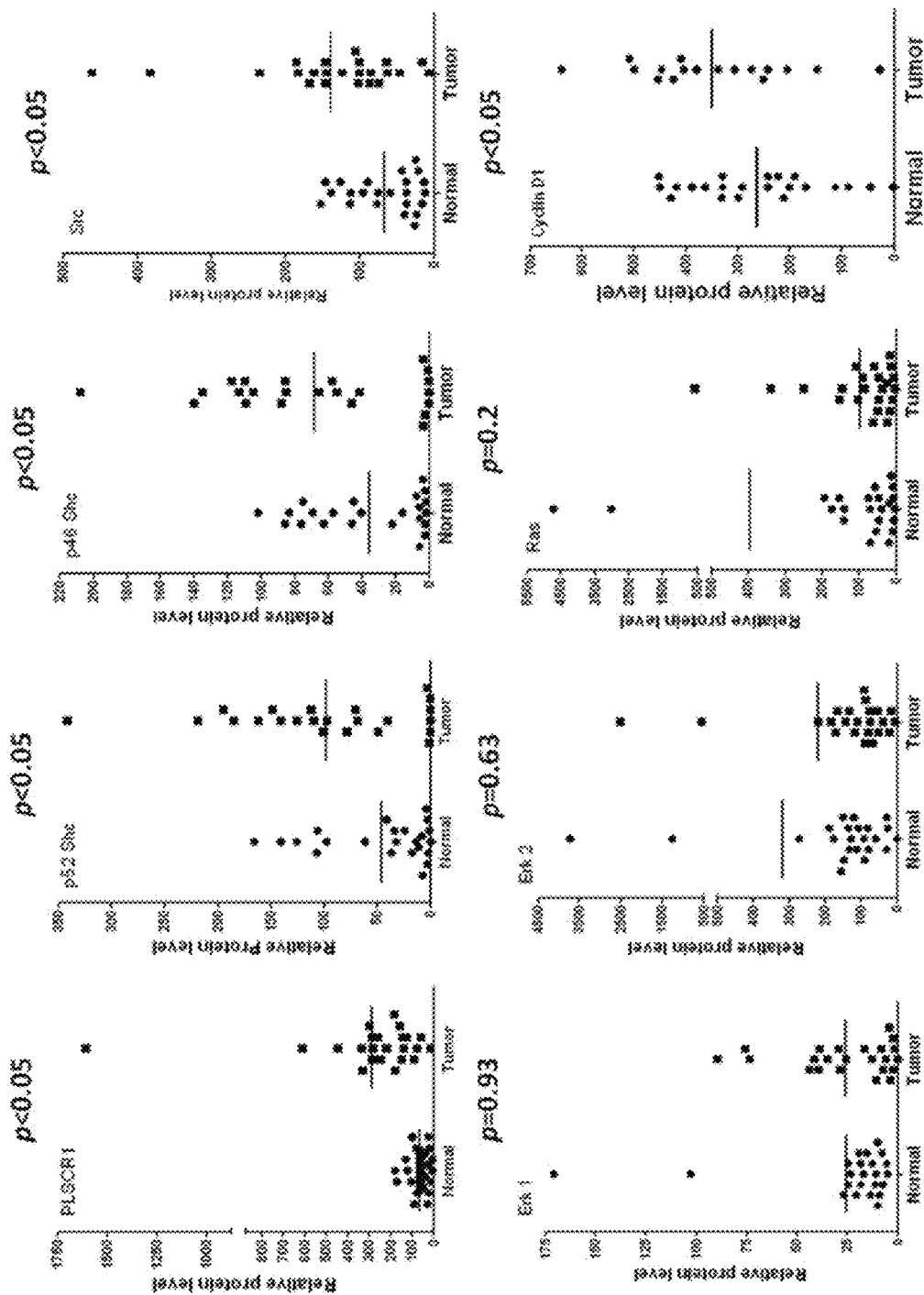
Figure 9:
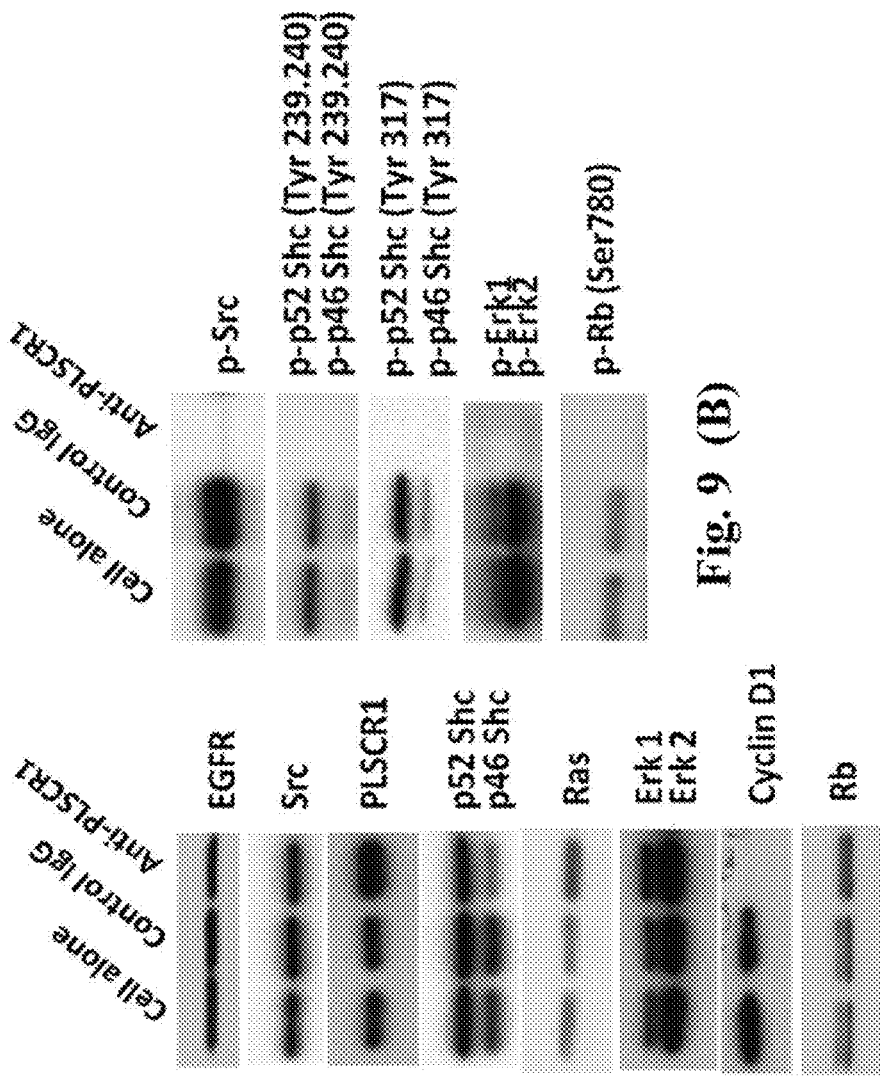
FIG. 9 Anti-PLSCR1 repressed cell proliferation through reactivation of the repressor Rb in HT29 cell line. (A) Anti-PLSCR1 repressed the expression of cyclin D1; and (B) Phosphorylation of Src, Shc, Erks and Rb decreased with anti-PLSCR1 treatment in HT29 cells.

Western blotting results implicated that PLSCR1, Shc, Src and cyclin D1 showed significantly differentially expression between tumor tissues and neighboring normal tissues (FIGS. 8(A)~(B)). On the other hand, results showed anti-PLSCR1 would repress the expression of cyclin D1 and the phosphorylation of Src, Shc, Erk, and Rb with anti-PLSCR1 treatment in HT29 cells (FIGS. 9(A)~(B)). Especially, Rb phosphorylation is decreased, but their expression didn't repress by anti-PLSCR1 treatment. It has been known that the un-phosphorylated form of Rb binds a member of E2F family of transcription factors which controls expression of several genes involved in cell cycle progression. Rb complex with E2F acts as a repressor, and this inhibits cells from progressing through G1. (Resnitzky D and Reed SI.1995).

Example 5

Binding Assays of Anti-PLSCR1 to Human Peripheral Blood Mononuclear Cells (PBMC) and Red Blood Cells (RBC)

Immunofluorescence Stain of PBMC and RBC Cells

The PBMC cells were harvested and washed three times with PBS. Cells were blocked with 2% bovine serum albumin (BSA) in PBS for 1 h at 4° C. The blocking reagent was removed and 10 μg/mL anti-PLSCR1 or HLA Class I antibody (W6/32, NOVUS BIOLOGICALS, USA) in PBS containing 5% BSA was added for 1 h. The antibody was removed and the cells were washed three times in PBS. The secondary Alexa Fluor® 488 Goat Anti-Mouse IgG (1:50; Invitrogen Taiwan Ltd., Taiwan) was added and incubated for 1 h. Cells were washed three times in PBS and 10,000 cells were counted by flow cytometry (EPICS XL-MCL, Beckman Coulter, USA). For the dose-dependent assays, PBMCs treated with 5, 10, and 20 μg/mL anti-PLSCR1 antibody were evaluated by flow cytometry as described above.

For human red blood cell (RBC) binding assays, human blood was diluted 1:500 in PBS. The diluted RBCs were incubated with 10 μg/mL of anti-PLSCR1 antibody or mouse anti-human CD47 antibody for 30 min at room temperature. The RBCs were washed three times in PBS. The secondary Alexa Fluor® 488 Goat Anti-Mouse IgG (1:50; Invitrogen Taiwan Ltd., Taiwan) was added and incubated for 30 min. Cells were washed three times in PBS and counted by flow cytometry (EPICS XL-MCL, Beckman Coulter, USA).

The results showed that the anti-PLSCR1 antibody was not significantly binding to PBMCs comparing with HLA Class I antibody, a positive control shown significant signal shift. Additionally, anti-PLSCR1 antibody also did not significantly bind to RBCs comparing with anti-human CD47 antibody. The result indicate that anti-PLSCR1 would not cause a binding or side effect to PBMCs and RBCs when intravenous administration at a concentration of 10 μg/mL. On the other hand, PBMCs or RBCs treated with 5, 10, and 20 μg/mL of anti-PLSCR1 shown similar signal shift, it didn't show a dose-dependent manner (FIGS. 11(A)~(D)).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for cancer therapy, which represses the activity of phospholipid scramblase 1 (PLSCR1) with a PLSCR1 monoclonal antibody, or binding fragment thereof, that specifically binds to the peptide of SEQ ID NO.2.

2. A method of treating cancer in a subject in need thereof, comprising administering to said subject a therapeutically effective amount of a PLSCR-inhibitor, wherein the PLSCR-inhibitor is a PLSCR1 monoclonal antibody, or binding fragment thereof, that specifically binds to the peptide of SEQ ID NO.2.

3. The method of claim 2, wherein the cancer exhibits the over-expression of PLSCR.

4. The method of claim 2, wherein the cancer is selected from breast cancer, hepatoma, colorectal cancer, pancreatic carcinoma, esophageal carcinoma, bladder cancer, ovarian cancer, skin cancer, gastric cancer, prostate cancer, lung cancer, renal cancer, thyroid cancer, brain cancer, melanoma, sarcoma, leukemia, bone cancer and endometrial cancer.

5. The method of claim 2, wherein the PLSCR-inhibitor is used to selectively target toxicity to cancer cells with high expression level of PLSCR.

6. The method of claim 5, which comprises exposing the cancer cells to a therapeutically effective amount of the PLSCR-inhibitor.

7. The method of claim 2, wherein the administration of the PLSCR-inhibitor is in combination with an additional therapy selected from radiation therapy, chemotherapy and immunomodulatory therapy.

8. The method of claim 1, wherein the cancer is colorectal cancer.

* * * * *